(12) United States Patent
Ronai

(10) Patent No.: US 7,935,525 B2
(45) Date of Patent: May 3, 2011

(54) INHIBITION OF ATF2 ACTIVITY TO TREAT CANCER

(75) Inventor: Ze'ev Ronai, San Diego, CA (US)

(73) Assignee: Mount Sinai School of Medicine, New York, NY (US)

( * ) Notice: Subject to any disclaimer, the term of this patent is extended or adjusted under 35 U.S.C. 154(b) by 174 days.

(21) Appl. No.: 11/945,133

(22) Filed: Nov. 26, 2007

(65) Prior Publication Data
US 2008/0139475 A1    Jun. 12, 2008

Related U.S. Application Data

(62) Division of application No. 10/076,905, filed on Feb. 14, 2002, now Pat. No. 7,314,855.

(60) Provisional application No. 60/269,257, filed on Feb. 16, 2001, provisional application No. 60/269,118, filed on Feb. 15, 2001.

(51) Int. Cl.
*C12N 15/00* (2006.01)

(52) U.S. Cl. ............... 435/320.1; 536/23.5; 530/300; 530/324; 530/350

(58) Field of Classification Search ............... 435/320.1; 536/23.1, 23.5; 530/300, 350, 324
See application file for complete search history.

(56) References Cited

U.S. PATENT DOCUMENTS

| 5,736,381 A | 4/1998 | Davis et al. ............... 435/252.3 |
| 6,335,178 B1 | 1/2002 | Weiner et al. ............... 435/69.1 |
| 6,579,856 B2 | 6/2003 | Mercola ........................ 514/44 |

OTHER PUBLICATIONS

Choi et al (J. Biol. Chem. Jul. 4, 1997; 272 (27): 16934-16939).*
Verma et al. (Nature 1997, 389: 239-242).*
Amalfitano et al. (Current Gene Therapy 2002, 2: 111-133).*
Pandha et al. (Current Opinion in Investigational Drugs 2000; 1 (1): 122-134).*
Ferrari et al. (Clin. Exp. Immunol. 2003; 132: 1-8).*
Zeimet et al. (Lancet. Jul. 2003; 4: 415-422).*
Riva (Anticancer Res. 2000; 20: 4463-4471).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Ahmed et al. (J. Immunol. 2006; 177: 315-321).
Crawford et al. (Annu. Rev. Genomics Hum. Genet. 2005; 6: 287-312).

GenBank™ Accession No. AAH26175 (Version AAH26175.1; GI:20072897).
GenBank™ Accession No. BC026175 (Version BC026175.1; GI:20072896).
Bailey et al. (J. Mol. Endocrinol. Feb. 2005; 34 (1): 19-35).
Jobling et al. (Plasmid. 1997; 38: 158-173).
Nilsson et al. (Nucleic Acid Res. 1985; 13 (4): 1151-1162).
Livingstone et al. (EMBO J. 1995; 14 (8): 1785-1797).
Abdel-Hafiz et al. (Mol. Endocrinol. Dec. 1992; 6 (12): 2079-2089).
Duyndam et al. (Oncogene. 1999; 18: 2311-2321).
Bhoumik et al. (Cancer Res. Nov. 15, 2004; 64: 8222-8230).
Bhoumik et al. (Proc. Natl. Acad. Sci USA. Mar. 23, 2004; 101 (12): 4222-4227).
Mi et al. (Mol. Ther. Oct. 2000; 2 (4): 339-347).
Cho et al., TIP49b, a Regulator of Activating Transcription Factor 2 Response to Stress and DNA damage. Mol. Cell. Biol. 2001. 21: 8398-8413.
Buschmann et al., Amino-terminal-derived JNK Fragment Alters Expression and Activity of c-Jun, ATF2, and p56 and Increases H2O2-Induced Cell Death, J. Biol. Chem. 2000; 278: 16590-96.
Duyndam MCA, et al. Oncogene. 1999; 18: 2311-21.
Gura T. Science. 1997; 278: 1041-42.
van Dam H, et al. EMBO J. Apr. 18, 1995; 14 (8): 1798-811.
Anindita Bhoumik et al., "An ATF2-Derived Peptide Sensitizes Melanomas to Apoptosis and Inhibits Their Growth and Metastasis," Sep. 2002, vol. 110, No. 5, pp. 643-650.
Anindita Bhoumik et al., "Transcriptional Switch by Activating Transcription Factor 2-Derived Peptide Sensitizes Melanoma Cells to Apoptosis and Inhibits Their Tumorigenicity," Mar. 23, 2004, vol. 101, No. 12, pp. 4222-4227.
Fritz et al., Journal of Biological Chemistry 1997; 272: 30637-30644 (abstract only).
Bhourmik et al., Clin. Cancer Res. 2001; 7(2):331-42.
Ivanov, V.N., and Ronai, Z., Oncogene 2000; 19: 3003-3012.
Ivanov, V.N. et al., Oncogene 2000; 19: 933-942.
Yang, Y.-M et al., Oncogene, 12 :2223-2233, 1996.
Ronai, Z. et al, Oncogene 1998; 16: 523-531.
Ivanov, V.N. et al., J. Biol. Chem. 1999; 274:14079-14089.
Gupta, S. et al., Science 1995; 267: 389-393.
Fuchs, S.Y. and Ronai, Z., Mol. Cell Biol. 1999; 19: 3289-3298.
Georgopoulos, K. et al., Mol. Cell. Biol.1992; 12: 747-757.
Huguier S. et al., Mol. Cell Biol. 1988; 18:7020-7029.

* cited by examiner

*Primary Examiner* — Stephen L Rawlings
(74) *Attorney, Agent, or Firm* — Fish & Richardson P.C.

(57) ABSTRACT

The present invention relates to novel therapies for cancer and, in particular, to therapies that are particularly suited to tumor cells resistant to other types of therapies such as radiation, chemotherapy, or combinations of both approaches. The invention provides methods for identifying and implementing strategies to inhibit a transcription factor which, in combination with other factors, renders the cells resistant and inhibits apopotosis of the cells. The invention provides an inhibitory ATF2 N-terminal fragment, specifically a fragment corresponding to amino acid residues 50-100 of ATF2 (termed peptide II). The invention provides methods for inhibiting tumor cell growth with such peptides.

6 Claims, 14 Drawing Sheets

Time After Tumor Injection (days)

Time After Tumor Injection (days)

Fig. 11A
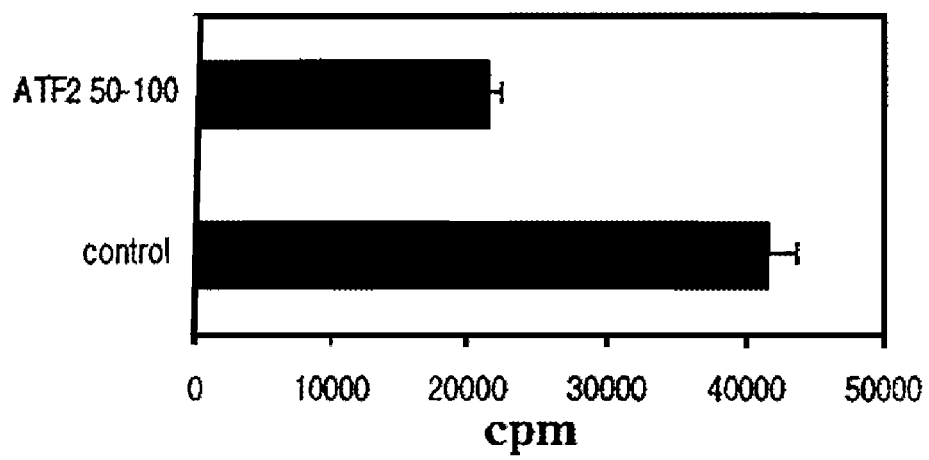
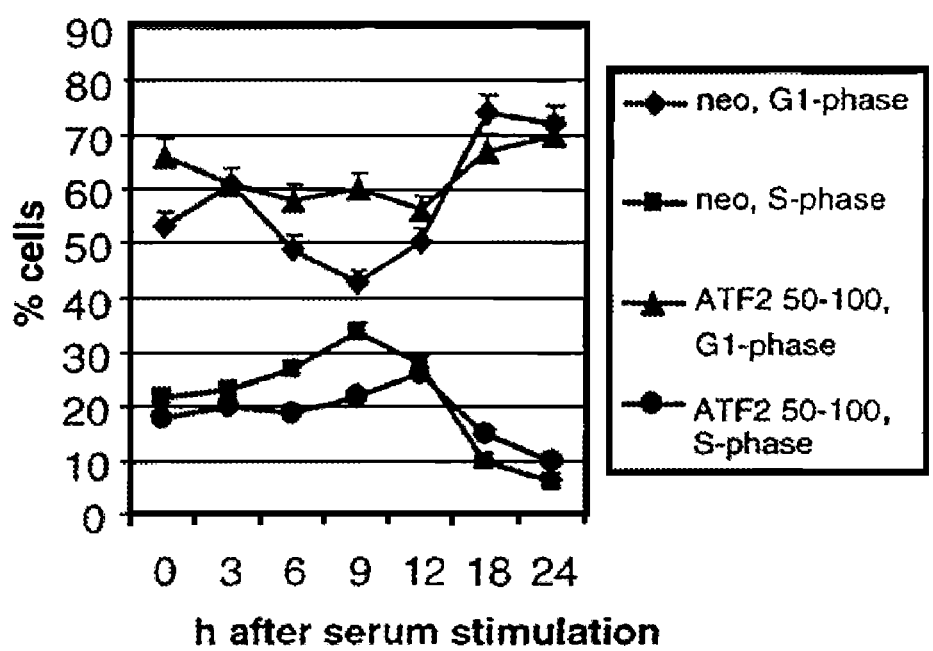
Fig. 11B

INHIBITION OF ATF2 ACTIVITY TO TREAT CANCER

This application is a divisional of prior application Ser. No. 10/076,905, filed Feb. 14, 2002, now U.S. Pat. No. 7,314,855; which claims priority under 35 U.S.C. 119(e) to U.S. provisional application Ser. No. 60/269,257, filed Feb. 16, 2001, and to U.S. Provisional Application Ser. No. 60/269,118, filed on Feb. 15, 2001. These applications are incorporated herein by reference in their entireties.

The research leading to the present invention was supported, in part, by the National Cancer Institute through grant CA 51995. Accordingly, the U.S. government has certain rights in the invention.

FIELD OF THE INVENTION

The present invention relates to therapy for cancer, particularly tumor cells that are resistant to radiation, chemotherapy, or both approaches. In particular, the invention relates to identification of strategies for inhibiting a transcription factor which, in combination with other factors, renders the cells resistant and inhibits apoptosis of the cells.

BACKGROUND OF THE INVENTION

The hallmark of malignant melanoma is its poor response to chemo- and radiotherapy. Despite advances in understanding of the biology of this tumor type (Meier et al., Frontiers in Bioscience 1998, 3: d1005-1010), the nature of melanoma's protection against radiation-induced apoptosis remains largely unknown. The ability to resist apoptosis by re-arranging the apoptosis machinery, including Fas, tumor necrosis factor receptor 1 (TNFR1), death receptor 3 (DR-3), TNF-related apoptosis-inducing ligand receptor 1 (TRAIL-R1) and TRAIL-R2 (Askenazi et al., Science 1998; 281:1305-1308; and, Nagata, S., Cell 1997; 88: 355-365), is characteristic of most tumor cells, including melanomas (Peli, J., et al., EMBO J. 1999; 18:1824-1831). Altered susceptibility to apoptosis was shown to include suppression of the death receptor or increased expression of inhibitory apoptosis proteins (IAP's) that restrain caspase activity (Deveraux, Q., et al., Genes & Dev. 1999; 13:239-252). Common to late-stage melanoma cells is the expression of a large subset of growth factors, cytokines and their respective receptors, which contribute to autocrine and paracrine regulation of their progression (Moretti, S., et al., Int. J. Cancer 1999; 20:160-168). Among the latter are TNF☐-TNFR1 and Fas-FasL, whose interaction elicits either death- or survival-signaling cascades. These cascades are regulated by the signal adaptor TNFR-associated factor2 (TRAF2) and its downstream effectors, i.e., stress activated kinases and their respective transcription factors (Hsu, H., et al., Cell 1996; 84:299-308; Liu, Z.-G., et al., Cell 1996; 87:565-576; Arch, R. H., et al., Gedrich, R. W., et al. and Genes & Dev. 1998; 12:2821-2830).

Key signaling molecules documented to play an important role in the biology of melanoma consists of cell adhesion molecules including cadherins, integrins, MUC18, ICAM (Johnson, J., Cancer Metastasis Rev. 1999; 18:345-357), MHC class I (Wang, R., J. Mol. Med. 1999; 77:640-655), PTEN and phospho-inositol 3 kinase (PI3K) (12-14), the Ras oncogene product (Jiveskog, S., et al., J. Invest. Dermatol. 1998; 5:757-761), the stress kinases Jun amino-terminal kinase (JNK) and p38 (Itoh, S., et al., J. Immunol. 1999; 162:7434-7440; Ivanov, V. N., et al., Oncogene 2000; 19:3003-3012), and their upstream regulator TRAF2 (Ivanov, V. N., et al., Oncogene 2000; 19:933-942), as well as signal-transducing molecules including ☐-catenin (Barker, N., et al., Adv Cancer Res. 2000; 77:1-24; Soldatenkov V A, et al., Cancer Res. 1999; 59:5085-8; Rubinfeld B, et al., Science 1997; 275:1790-2), and cell cycle regulators such as p16 (Piepkorn, M., J. Am. Acad. Dermatol. 2000; 42:705-726). Either mutation or altered expression has been reported for these regulatory proteins, which confer the changes implicated in the development and progression of human melanoma.

In comparing early- and late-stage melanoma cells we identified lower expression and activities of TRAF2 and its respective effectors germinal center kinase (GCK) and nuclear factor-kB (NF-kB) in early-stage melanoma cells (Ivanov, V. N., et al., Oncogene 2000; 19:933-942). Low expression levels of TRAF2/GCK in early-stage melanoma cells coincide with low level of c-Jun and NF-kB activities. Forced expression of GCK in these cells efficiently increased the resistance of the early-phase melanoma to radiation. Similarly, expression of the dominant negative form of GCK in late-stage melanoma reduced the resistance of late-phase melanoma cells lines to radiation (Ivanov, V. N., et al., Oncogene 2000; 19:933-942). These observations pointed to the changes in the regulation of key stress signaling molecules during melanoma progression and to the role of TRAF2 and its effector GCK in acquiring radiation resistance of late-phase human melanoma cells.

In elucidating transcription factors that may alter melanoma's resistance to UV-irradiation, we identified CREB associated proteins (Yang, Y.-M., et al., Oncogene 1996; 12:2223-2233) among which ATF2 was found to play an important role in acquiring such resistance (Ronai, Z., et al., Oncogene 1998; 16:523-531). Hypophosphorylated or transcriptionally inactive forms of ATF2 elicit a silencing effect on TNF☐ expression, which mediates an anti-apoptotic signal in LU1205, a late-stage melanoma cell line, resulting in increased apoptosis (Ivanov, V. N., et al., J. Biol. Chem. 1999; 274:14079-14089). The importance of the p38 signaling cascade, which is among major ATF2 kinases, in the biology of human melanoma was further demonstrated by the finding that p38 negatively regulates the expression of Fas via suppression of NF-kB transcriptional activity (Ivanov, V. N., et al., Oncogene 2000; 19:3003-3012). Thus, p38 appear to play a key role in acquiring the resistance of melanoma to radiation-induced apoptosis through its ATF2 effector, which upregulates TNFα expression, and via p38 direct suppression of NF-kB, which down-regulates Fas expression.

SUMMARY OF THE INVENTION

In one aspect, the invention advantageously provides a method of inhibiting growth of a tumor cell. This method comprises inhibiting transcriptional activity of ATF2. Inhibition of transcriptional activity of ATF2 can include introducing a polypeptide comprising an N-terminal antagonist fragment of ATF2 into the tumor cell. For example, the N-terminal fragment of ATF2 comprises amino acid residues from about residue 45 of ATF2 to about 100 of ATF2, or amino acid residues from about residue 50 of ATF2 to about 100 of ATF2 (hereinafter peptide II). In a specific embodiment, introducing the polypeptide comprising an N-terminal antagonist fragment of ATF2 into the tumor cell comprises introducing an expression vector encoding the polypeptide into the tumor cell under conditions that permit expression of the polypeptide from the vector.

The method of the invention has been specifically exemplified in conditions where the tumor cell is a melanoma tumor cell or a breast cancer tumor cell.

Preferably, the method of inhibiting tumor cell growth involves treating the tumor cell with a chemotherapeutic agent, such as but not limited to a p38 inhibitor, UCN-01, NCS, anisomycin, LY294002, PD98059, AG490, and SB203580. Alternatively, the invention contemplates further treating the tumor cell with radiation.

In a specific aspect, the invention provides a polypeptide comprising a sequence from about amino acid residue 50 to about amino acid residue 75 of ATF2, more particularly from about amino acid residue 45 to about amino acid residue 100 of ATF2. In specific embodiments, the peptides consist of amino acid residues 50-100 (peptide II), 45-75, and 1-115. Preferably, for delivery to the interior of cells in vivo, the polypeptide further comprises a translocation peptide sequence. Naturally, the invention provides nucleic acids and expression vectors encoding such polypeptides.

For treatment, the invention provides a pharmaceutical composition comprising the polypeptide of the invention, or an expression vector of the invention, and a pharmaceutically acceptable carrier or excipient. Such pharmaceutical compositions can be used in a method of treating a tumor in a subject, as set forth above in connection with inhibiting growth of a tumor cell.

In addition, the invention provides a method for identifying a compound that modulates ATF2 activity. This method comprises determining the level of expression of a reporter gene in a cell comprising the reporter gene operatively associated with an ATF2-regulated expression control sequence contacted with a compound under conditions in which ATF2 would induce expression of the reporter gene in the absence of the compound, and comparing the level of expression of the reporter gene in the presence of the compound to the level of expression in the absence of the compound, wherein a difference in the level of expression of the reporter gene indicates that the compound modulates ATF2 activity. In a specific embodiment, the level of reporter gene expression in the presence of the compound is less than in the absence of the compound, wherein the compound inhibits ATF2 activity. In another specific embodiment, the compound is a polypeptide.

DESCRIPTION OF THE DRAWINGS

FIG. 2C depicts resistance of LU1205 cells to the radiomimetic drug NCS. In 2C, the first (solid) bar is for neo-expressing LU1205 cells; the second (horizontal stripe) bar is peptide-II expressing LU1205 cells; and the third (stippled) bar is peptide IV-expressing LU1205 cells. FIG. 2D show sensitivity (measured via degree of apoptosis) of LU1205 cells to treatment with either Adriamycin® (ADR 20 mM) alone or in combination with multi-drug resistance MDR inhibitor verapamil (Ver, 1 mM). The bars in 2D are the same as in 2C.

FIG. 5C shows the analysis of apoptosis in human melanocytes (FOM71) performed 36 h after exposure to UV (75 J/m$^2$), SB203580 (100M) or NCS (100 ng/ml). Analysis was carried out in triplicate and each experiment reproduced twice. In each set of bars, the first (solid) bars are for neo-expressing controls, the second (striped) bars are for peptide-II expressing FOM71 cells; and the third (open) bars are for peptide IV-expressing FOM71 cells.

FIG. 10A is a graphical representation of tumor growth up to 25 days post-injection (P<0.0001) and 10B shows a survival curve delineating the effect of expression of peptide II on survival of the mice for each protocol. The first curve (from left to right) is for a solution control, the middle curve is for a control adenovirus, and the last curve is for adenovirus expressing peptide II.

FIG. 11A shows results of the analysis of changes in growth rate of cells that express the ATF2 peptide as measured by thymidine incorporation.

FIG. 11B shows results from analysis of cell cycle distribution of peptide II-expressing cells or control cells after synchronization followed by stimulation with serum.

Figure 1A:
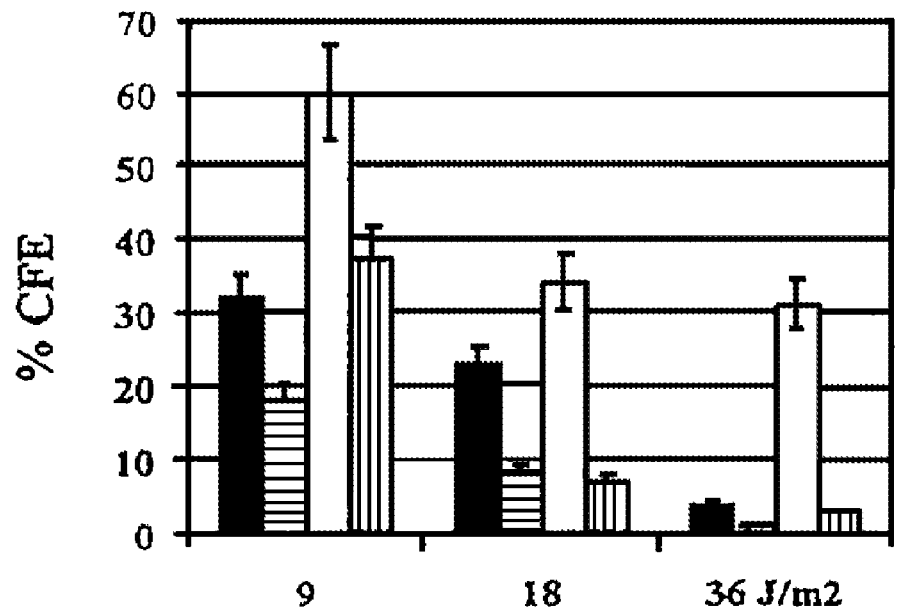
FIGS. 1A and 1B. Altered resistance of melanoma cells expressing ATF2-derived peptides to UV-irradiation. Colony forming efficiency (CFE) of LU1205 or FEMX melanoma cell lines expressing ATF2-derived peptide II (FIG. 1A) or peptide IV (FIG. 1B) was carried out 14 days after exposure to the indicated doses (9, 18, or 36 J/m$^2$) of UV-C (254 nm). In all cases analysis was performed on triplicate wells and reproduced at least 3 times. Percent of CFE shown is calculated over the respective control cell lines transfected with the empty vector (neo). In each data set, the first (solid) bar is for neo-expressing LU1205 cells; the second (horizontal stripe) bar is for peptide-expressing LU1205 cells; the third (light stipple) bar is for neo-expressing FEMX cells; and the fourth (cross-hatch) bar is for peptide-expressing FEMX cells.

( —□— )represents the percentage of control cells in the G1 phase of the cell cycle, while ( (—■—)) represents the percentage of peptide II-expressing cells in G1.

( —□— )represents the percentage of control cells in the S phase of the cell cycle, while ( (—■—)) represents the percentage of peptide II-expressing cells in S phase.

DETAILED DESCRIPTION

The present invention advantageously provides an approach for inhibiting growth of tumor cells, and particularly for rendering tumor cells susceptible to radiation or chemotherapy. In particular, inhibition of ATF2 activity results in growth inhibition of tumor cells, and enhances anti-tumor activity of radiation and chemotherapeutic drugs.

ATF2 and its kinase, p38, play an important role in melanoma's resistance to radiation and chemotherapy. Whereas ATF2 upregulates the expression of TNFα, which serves as a survival factor in late-stage melanoma cells, p38 attenuates Fas expression via inhibition of NF-κB. The present invention is based, in part, on an investigation of whether ATF2-derived peptides could be used to alter the sensitivity of human melanoma cells to radiation and chemical treatment. Of four 50 amino acid peptides tested, the peptide spanning amino acid residues 50-100 elicits the most efficient increase in the sensitivity of human melanoma cells to UV radiation or treatment by mitomycin C, Adriamycin® and verapamil, or UCN-01, as revealed by apoptosis assays. Sensitization by ATF2 peptide was also observed in the MCF7 human breast cancer cells, but not in early-stage melanoma, or melanocytes, or in in vitro transformed 293T cells. When combined with an inhibitor of the p38 catalytic activity, cells expressing the 50-100 fragment of ATF2 exhibited an increase in the degree of programmed cell death, indicating that combined targeting of ATF2 and p38 kinases is sufficient to induce apoptosis in late-stage melanoma cells. The peptide's ability to increase levels of apoptosis coincided with increased cell surface expression of Fas, which is the primary death-signaling cascade in these late stage melanoma cells. Overall, our studies identify a critical domain of ATF2, which may be used to sensitize tumor cells to radiation and chemical treatment-induced apoptosis and which can induce apoptosis, when combined with inhibition of ATF2 kinase, p38.

Thus, the invention advantageously provides a method for treating a mammal suffering from a tumor, in which the cells of the tumor are resistant to apoptosis, radiation, or chemotherapeutic agents, or any combination of the foregoing.

The invention specifically provides three strategies for inhibiting ATF2: use of ATF2 inhibitory peptides, use of ATF2 inhibitory vectors, and use of ATF2 antisense oligonucleotides (particularly nucleotide analogs). Either approach can be used therapeutically. The peptide-based approach involves delivering an inhibitory N-terminal fragment of ATF2 to cells, or delivery of an anti-ATF2 antibody with inhibitory activity to cells. In a preferred embodiment, the polypeptide (ATF2 inhibitory fragment or antibody) enters the cell with the assistance of a translocation peptide sequence. The vector based approach involves delivering a vector comprising an gene encoding and ATF2 inhibitor, such as the inhibitory ATF2 N-terminal fragment, an anti-ATF2 antibody with inhibitory activity, or an ATF2 anti-sense nucleic acid, As used herein, the term "inhibitory ATF2 N-terminal fragment" refers to an N-terminal polypeptide fragment of ATF2 that inhibits ATF2 activity, and which excludes full-length ATF2. Based on the ability of specific fragments to mediate ATF2 inhibition, the inhibitor fragment comprises from about amino acid residue 50 to about amino acid residue 75, i.e., about a 25 amino acid peptide. In exemplified embodiments, a 30 amino acid residue peptide (45-75), a 50 amino acid residue peptide (50-100), and a 115 amino acid residue peptide (1-115) were found to inhibit ATF2 activity. In exemplified embodiments, the inhibitory peptides were introduced into tumor cells through expression vectors.

"Peptide II" refers to an N-terminal polypeptide fragment of ATF2 that comprises amino acid residues 50-100 and which inhibits ATF2 activity. Peptide II is used herein interchangeably with "ATF2 peptide" and ATF2$^{50-100}$.

"Inhibition of ATF2 activity" (and all grammatical variations thereof) includes, but is not limited to, inhibition of ATF2-regulated transcription; inhibition of tumor cell growth (relative to untreated tumor cells); an increase in apoptosis; an increase in the sensitivity of tumor cells, particularly human melanoma and breast cancer cells, to UV radiation or treatment by chemotherapeutic drugs such as mitomycin C, Adriamycin® and verapamil, and UCN-01; and the like. In particular, inhibition of ATF2 activity comprises inhibiting growth of a tumor cell, which method comprises inhibiting transcriptional activity of ATF2.

As used herein, the term "tumor" refers to a malignant tissue comprising transformed cells that grow uncontrollably. Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

As used herein, the term "mammal" has its ordinary meaning, and specifically includes primates, and more specifically includes humans. Other mammals that may be treated for the presence of a tumor, or in which tumor cell growth may be inhibited, include, but are not limited to, canine, feline, rodent (racine, murine, lupine, etc.), equine, bovine, ovine, caprine, and porcine species.

"Gene therapy" refers to transfer of a gene encoding an effector molecule into cells, in this case of the tumor. Gene therapy vectors include, but are not limited to, viral vectors (including retroviruses and DNA viruses), naked DNA vectors, and DNA-transfection agent admixtures. Such methods, including routes of administration and dose, are well known in the art.

Translocation Peptide Sequences

Peptide sequences have been identified that mediate membrane transport, and accordingly provide for delivery of polypeptides to the cytoplasm. For example, such peptides can be derived from the antennapedia homeodomain helix 3 to generate membrane transport vectors, such as penetratin (PCT Publication WO 00/29427; see also Fischer et al., J. Pept. Res. 2000, 55:163-72; DeRossi et al., Trends in Cell Biol. 1998, 8:84-7; Brugidou et al., Biochem. Biophys. Res. Comm. 1995, 214:685-93). Protein transduction domains, which include the antennapedia domain and the HIV TAT domain (see Vives et al., J. Biol. Chem. 1997, 272:16010-17), posses a characteristic positive charge, which led to the development of cationic 12-mer peptides that can be used to transfer therapeutic proteins and DNA into cells (Mi et al., Mol. Therapy. 2000, 2:339-47).

Therapeutic polypeptides can be generated by creating fusion proteins or polypeptide conjugates combining a translocation peptide sequence with a therapeutically functional sequence. For example, p21$^{WAF1}$-derived peptides linked to a translocation peptide inhibited ovarian tumor cell line growth (Bonfanti et al., Cancer Res. 1997, 57:1442-1446). These constructs yield more stable drug-like polypeptides able to penetrate cells and effect a therapeutic outcome. These constructs can also form the basis for rational drug design approaches.

In a specific embodiment of the invention, polypeptides comprising peptide translocation sequences (preferably at the N-terminal region of the polypeptide) and an ATF2 inhibitory fragment of ATF2, preferably comprising amino acids from about residue 50 to about residue 100 of ATF2, are prepared. They can be prepared synthetically or by genetic engineering. These polypeptides are the preferred embodiment of "ATF2 inhibitory polypeptides" of the invention.

An alternative approach employs an anti-ATF2 antibody fused or conjugated to a peptide translocation sequence, which can be administered systemically for intracellular activity. Preferably such an anti-ATF2 antibody is a single chain Fv antibody.

ATF2 Inhibitory Antibodies

Intracellular antibodies (sometime referred to as "intrabodies") have been used to regulate the activity of intracellular proteins in a number of systems (see, Marasco, Gene Ther. 1997, 4:11; Chen et al., Hum. Gene Ther. 1994, 5:595), e.g., viral infections (Marasco et al., Hum. Gene Ther. 1998, 9:1627) and other infectious diseases (Rondon et al., Annu. Rev. Microbiol. 1997, 51:257), and oncogenes, such as p21 (Cardinale et al., FEBS Lett. 1998, 439:197-202; and Cochet et al., Cancer Res. 1998, 58:1170-6), myb (Kasono et al., Biochem Biophys Res Commun. 1998, 251:124-30), erbB-2 (Graus-Porta et al., Mol Cell Biol. 1995, 15:1182-91), etc. This technology can be adapted to inhibit ATF2 activity by expression of an anti-ATF2 intracellular antibody.

Alternatively, monoclonal antibodies directed toward the ATF2 polypeptide, or fragment, analog, or derivative thereof, may be used, provided they are directed into the cytoplasm of the cell to bind and inhibit ATF2. Methods of obtaining such antibodies include but are not limited to the hybridoma technique originally developed by Kohler and Milstein (Nature 1975, 256:495-497), as well as the trioma technique, the human B-cell hybridoma technique (Kozbor et al., Immunology Today 1983, 4:72; Cote et al., Proc. Natl. Acad. Sci. USA 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (PCT Publication No. WO 89/12690). In fact, according to the invention, techniques developed for the production of "chimeric antibodies" (Morrison et al., J. Bacteriol. 1984, 159:870; Neuberger et al., Nature 1984, 312:604-608; and Takeda et al., Nature 1985, 314:452-454) by splicing the genes from a mouse antibody molecule specific for an ATF2 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. No. 4,946,778) can be adapted to produce ATF2 polypeptide-specific single chain antibodies. Indeed, these genes can be delivered for expression in vivo. An additional embodiment of the invention utilizes the techniques described for the construction of Fab expression libraries (Huse et al., Science 246:1275-1281, 1989) to allow rapid and easy identification of monoclonal Fab fragments with the desired specificity for an ATF2 polypeptide, or its derivatives, or analogs. Single chain antibodies (which for the basis for most intrabody technology) are preferred, particularly those engineered to express a peptide translocation sequence.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

ATF2 Inhibitory Nucleic Acids

In addition to ATF2 inhibitory vectors, which are described in detail below, the present invention contemplates that antisense nucleic acids, such as DNA, RNA, nucleic acid analogs (as described below) and the like can be used to inhibit ATF2 activity, specifically by inhibiting expression of ATF2.

Molecular Biology—Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, caps substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

Promoters which may be used to control gene expression include, but are not limited to, elongation factor promoter from polyoma virus, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. USA 1981, 78:1441-1445), the regulatory sequences of the metallothionein gene (Brinster et al., Nature 1982, 296:39-42); prokaryotic expression vectors such as the beta-lactamase promoter (Villa-Komaroff, et al., Proc. Natl. Acad. Sci. USA 1978, 75:3727-3731), or the tac promoter (DeBoer, et al., Proc. Natl. Acad. Sci. USA 1983, 80:21-25); see also "Useful proteins from recombinant bacteria" in Scientific American 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 1985, 315:338-340; Kollias et al., Cell 1986, 46:89-94), hematopoietic stem cell differentiation factor promoters, erythropoietin receptor promoter (Maouche et al., Blood 1991, 15:2557), etc. Inducible/repressible promoter systems can also be used, such as the tet, RU 486, and echdysone inducible systems, and the tet repressor system.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" transcriptional and translational control sequences in a cell when RNA polymerase transcribes the coding sequence into RNA, particularly mRNA, which is then trans-RNA spliced (if it contains introns) and translated into the protein encoded by the coding sequence.

The terms "vector", "cloning vector" and "expression vector" mean the vehicle by which a DNA or RNA sequence (e.g.

a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clontech®), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

The term "expression system" means a host cell and compatible vector under suitable conditions, e.g. for the expression of a protein coded for by foreign DNA carried by the vector and introduced to the host cell. Common expression systems include $E.\ coli$ host cells and plasmid vectors, insect host cells and Baculovirus vectors, and mammalian host cells and vectors. In a specific embodiment, the protein of interest is expressed in COS-1 or $C_2C_{12}$ cells. Other suitable cells include CHO cells, HeLa cells, 293T (human kidney cells), mouse primary myoblasts, and NIH 3T3 cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed, e.g., a CHO cell.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function—conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., Cell 50:667, 1987). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95%) of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, *Version* 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55□C. can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55□C, and utilizes conditions as set forth above. In a preferred embodiment, the $T_m$ is 60□C.; in a more preferred embodiment, the $T_m$ is 65□C. In a specific embodiment, "high stringency" refers to hybridization and/or washing conditions at 68□C in 0.2×SSC, at 42□C in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids encoding the protein. In a further embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of a target protein of the invention. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. Nos. 5,814,500; 5,811, 234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 1991, 254:1497). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

Expression Vectors

Preferred vectors in vitro, in vivo, and ex vivo are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication WO 95/28494.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 1992, 7:980-990). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

The gene can be introduced in a retroviral vector, e.g., as described in Anderson et al., U.S. Pat. No. 5,399,346; Mann et al., Cell 1983, 33:153; U.S. Pat. Nos. 4,650,764, 4,980,289, and 5,124,263; Markowitz et al., J. Virol. 1988, 62:1120; and Temin et al., U.S. patent No.; EP 453242, EP178220; Bernstein et al. Genet. Eng. 1985, 7:235; McCormick, BioTechnology 1985, 3:689; PCT; and Kuo et al., 1993, Blood 82:845. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (PCT Publication No. WO 90/02806) and the GP+envAm-12 cell line (PCT Publication No. WO 89/07150). Retrovirus vectors can also be introduced by DNA viruses, which permits one cycle of retroviral replication and amplifies transfection efficiency (see PCT Publication Nos. WO 95/22617, WO 95/26411, WO 96/39036, WO 97/19182).

In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest (see, Naldini, Curr. Opin. Biotechnol., 9:457-63, 1998; see also Zufferey, et al., J. Virol., 72:9873-80, 1998; Kafri, et al., J. Virol., 73: 576-584, 1999).

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective After introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991, 2:320-330), defective herpes virus vector lacking a glycoprotein L gene (Patent Publication RD 371005 A), or other defective herpes virus vectors (PCT Publication Nos. WO 94/21807 and WO 92/05263); an attenuated adenovirus vector, such as the vector described by Stratford-Perricaudet et al. (J. Clin. Invest. 1992, 90:626-630; see also La Salle et al., Science 1993, 259:988-990; various replication defective adenovirus and minimum adenovirus vectors have been described in PCT Publication Nos. WO 94/26914, WO 95/02697, WO 94/28938, WO 94/28152, WO 94/12649, WO 95/02697, and WO 96/22378); and a defective adeno-associated virus vector (Samulski et al., J. Virol. 1987, 61:3096-3101; Samulski et al., J. Virol. 1989, 63:3822-3828; Lebkowski et al., Mol. Cell. Biol. 1988, 8:3988-3996; PCT Publication Nos. WO 91/18088 and WO 93/09239; U.S. Pat. Nos. 4,797,368 and 5,139,941; European Publication No. EP 488 528).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-□ (IFN-□), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Various companies produce viral vectors commercially, including but by no means limited to Avigen, Inc.® (Alameda, Calif.; AAV vectors), Cell Genesys® (Foster City, Calif.; retroviral, adenoviral, AAV vectors, and lentiviral vectors), Clontech® (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene™ (Strasbourg, France; adenoviral, vaccinia, retroviral, and lentiviral vectors).

In another embodiment, the vector can be non-viral. Such vectors include "naked" DNA, and transfection facilitating agents (peptides, polymers, etc.). Synthetic cationic lipids can be used to prepare liposomes for transfection of a gene encoding (Felgner, et. al., Proc. Natl. Acad. Sci. U.S.A. 84:7413-7417, 1987; Felgner and Ringold, Science 337:387-388, 1989; see Mackey, et al., Proc. Natl. Acad. Sci. U.S.A. 85:8027-8031, 1988; Ulmer et al., Science 259:1745-1748, 1993). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et. al., Proc. Natl. Acad. Sci. U.S.A. 85:8027-8031). Targeted peptides, e.g., hormones or neurotransmitters, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 267:963-967, 1992; Wu and Wu, J. Biol. Chem. 263: 14621-14624, 1988; Hartmut et al., Canadian Patent Application No. 2,012,311, filed Mar. 15, 1990; and Williams et al., Proc. Natl. Acad. Sci. USA 88:2726-2730, 1991). Receptor-mediated DNA delivery approaches can also be used (Curiel et al., Hum. Gene Ther. 3:147-154, 1992; and Wu and Wu, J. Biol. Chem. 262:4429-4432, 1987). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci., 321:893, 1998; WO 99/01157; WO 99/01158; and WO 99/01175).

ATF2 Inhibitor Therapy

As noted above, ATF2 inhibition strategies can be used to treat any cancer in which tumor cells demonstrate resistance to apoptosis, radiation, chemotherapeutic agents, or any combination of the foregoing. Moreover, ATF2 inhibition provides first or second (or later) line approach to cancer therapy, and can be used alone or preferably in combination with a traditional therapeutic approach, e.g., chemotherapy or radiation.

ATF2 inhibitory polypeptides or ATF2 inhibitor vectors as described above can be formulated in a pharmaceutical composition for administration to a patient. As used herein, a "pharmaceutical composition" includes the active agent, i.e., the polypeptide or vector, and a pharmaceutically acceptable carrier, excipient, or diluent. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

For human therapy, the pharmaceutical compositions, including each of the active agents, will be prepared in accordance with good manufacturing process (GMP) standards, as set by the Food & Drug Administration (FDA). Quality assurance (QA) and quality control (QC) standards will include testing for purity and function, in the case of polypeptides; homogeneity and function in the case of vectors; and the presence of replication competent virus (if the virus vector is defective) for viral vectors; and other standard measures.

In order to treat the tumor cells, the pharmaceutical composition is administered by any route that will permit delivery of the active agent to the tumor cells. Since inhibition of ATF2 activity does not appear to harm normal (non-transformed) cells, systemic administration of the active agent is acceptable. Preferably, administration is parenteral, e.g., via intravenous injection, and also including, but is not limited to, intra-arteriole, intramuscular, intradermal, subcutaneous, intraperitoneal, intraventricular, and intracranial administration. Indeed, one of the advantages of this invention is that the specificity of the ATF2 inhibitor for transformed cells means that the active agent will affect metastatic cells, even micrometastasises that cannot be resected or located by standard techniques (CAT scanning, MRI scanning, etc.). Alternatively, particularly when the active agent is a therapeutic vector, delivery is locally to the tumor.

In therapeutic treatments of the invention, the physician will administer a therapeutically effective amount of the pharmaceutical composition. As used herein, the term "therapeutically effective amount" means an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. Specifically, a therapeutically effective amount will cause one or more of the following: apoptosis of tumor cells; necrosis of tumor cells; elimination or prevention of tumor metastasises; reduction in the rate of tumor growth; reduction in tumor size or tumor shrinkage; elimination of the tumor; remission of the cancer; an increase in the time for reappearance of the cancer; and increased time of survival of the patient. The frequency and dosage of the therapy can be titrated by the ordinary physician using standard dose-to-response techniques.

Combination Therapies

The therapeutic compositions of the invention can be used in combination with other anti-cancer strategies, as disclosed herein. In particular, as noted above, a particular advantage of ATF2 inhibition in accordance with the invention results from the adjuvant effect of this strategy on traditional tumor therapies. Although the methods of the invention are effective in inhibiting tumor growth and metastasis, the vectors and methods of the present invention are advantageously used with other treatment modalities, including without limitation radiation and chemotherapy. In particular, ATF2 inhibition can be administered with a chemotherapeutic such as, though not limited to, a p38/JAK kinase inhibitor, e.g., SB203580; a phospatidyl inositol-3 kinase (PI3K) inhibitor, e.g., LY294002; a MAPK inhibitor, e.g., PD98059; a JAK inhibitor, e.g., AG490; preferred chemotherapeutics such as UCN-01, NCS, mitomycin C (MMC), NCS, and anisomycin; taxoids such as Taxol®, Taxotere® and other taxoids (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publication Nos. WO 91/17976, WO 93/00928, WO 93/00929, and WO 96/01815), or other chemotherapeutics, such as cis-platin (and other platin intercalating compounds), etoposide and etoposide phosphate, bleomycin, mitomycin C, CCNU, doxorubicin, daunorubicin, idarubicin, ifosfamide, and the like.

The term "anti-tumor gene therapy" as used herein refers to a gene therapy targeted to a tumor, which causes tumor necrosis, apoptosis, growth regulation, i.e., regression or suppression of the tumor. Examples of anti-tumor gene therapies (in addition to delivery of an ATF2 inhibitor vector as set forth above) include, but are by no means limited to, introduction of a suicide gene; introduction of an apoptosis gene; introduction of a tumor suppresser gene; and introduction of an oncogene antagonist gene. Preferably anti-tumor genes are supplemented with immunostimulatory genes to enhance recruitment and activation of immune effector cells, including mobilized dendritic cells, to the tumor.

Suicide gene therapies. Introduction of genes that encode enzymes capable of conferring to tumor cells sensitivity to chemotherapeutic agents (suicide gene) has proven to be an effective anti-tumor gene therapy. The present invention provides a method of treating cancer in part by introducing a gene vector, encoding a protein capable of enzymatically converting a prodrug, i.e., a non-toxic compound, into a toxic compound. In the method of the present invention, the therapeutic nucleic acid sequence is a nucleic acid coding for a product, wherein the product causes cell death by itself or in the presence of other drugs. A representative example of such a therapeutic nucleic acid is one which codes for thymidine kinase of herpes simplex virus. Additional examples are thymidine kinase of varicella zoster virus and the bacterial gene cytosine deaminase which can convert 5-fluorocytosine to the highly toxic compound 5-fluorouracil.

The prodrug useful in the methods of the present invention is any that can be converted to a toxic product, i.e., toxic to tumor cells. The prodrug is converted to a toxic product by the gene product of the therapeutic nucleic acid sequence in the vector useful in the method of the present invention. Representative examples of such a prodrug is ganciclovir, which is converted in vivo to a toxic compound by HSV-tk. The ganciclovir derivative is toxic to tumor cells. Other representative examples of pro-drugs include acyclovir, FIAU [1-(2-deoxy-2-fluoro-beta-D-arabinofuranosyl)-5-iodouracil], 6-methoxypurine arabino-side for VZV-tk, and 5-fluorocytosine for cytosine deambinase.

Ganciclovir, or any of the pro-drugs, may be readily administered by a person having ordinary skill in this act. A person with ordinary skill would readily be able to determine the most appropriate dose and route for the administration of ganciclovir. Preferably, ganciclovir is administered in a dose of from about 1-20 mg/day/kg body weight. Preferably, acyclovir is administered in a dose of from about 1-100 mg/day/kg body weight and FIAU is administered in a dose of from about 1-50 mg/day/kg body weight.

HSV-tk based immunotherapy is built upon the fact that expression of the TK gene in conjunction with the drug ganciclovir (GCV) induces conditional toxicity in a transfected local tumor in addition to immune mediated inflammation (Chen et. al., Cancer Res. 1996, 56: 3758-3762).

Anti-oncogene and tumor suppresser gene therapies. Tumor initiation and progression in many cancer types are linked to mutations in oncogenes (e.g., ras, myc) and tumor suppresser genes (e.g., retinoblastoma protein, p53). A number of approaches are being pursued using anti-oncogene molecules including monoclonal antibodies, single chain antibody vectors, antisense oligonucleotide constructs, ribozymes and immunogenic peptides (Chen, Mol. Med. Today 1997, 3:160-167; Spitz, et al., Anticancer Res. 1996, 16:3415-3422; Indolfi et al., Nat. Med. 1996, 2:634-635; and Kijima et al., Pharmacol. Ther. 1995, 68:247-267). These molecules specifically inhibit the function of these molecules, suppress tumor growth and increase the apoptosis rate in tumor cells. These mechanisms require constant presence of the suppresser or anti-oncogene molecules for sustained responses. However, these mechanisms by themselves have not been shown to induce tumor specific immunity, which has the potential of memory necessary for protection against the recurrence of the disease. Combination of these tumor growth specific strategies with DC mobilization will have a synergistic effects on tumor regression and induction of protective immune response.

Accordingly, in another embodiment, gene therapy for tumors includes but is by no means limited to p53 (PCT Publication No. WO 94/24297) or analogues thereof such as CTS-1 (French Patent Application No. FR 08729), anti-RAS single chain antibodies or antisense molecules (PCT Publication No. WO 97/16547), interferon-alpha or interferon-gamma, etc., as described above. Any vector for gene therapy can be used in conjunction with the present invention, such as a viral vector or naked DNA.

Immunostimulatory therapies. The invention can provides for immune cell stimulation, such as dendritic cell mobilization, to generate a strong anti-tumor immune response. Immunostimulatory molecules include flt-3 ligand (flt-3L), granuclocyte-macrophage colony stimulating factor (GM-CSF), interleukin (IL)-12 and IL-13, IL-2, and IL-7. Other such cytokines include, but are not limited to, IL-3, and IL-4, a colony stimulating factor ("CSF") selected from the group consisting of granulocyte macrophage colony stimulating factor ("GM-CSF") or GM-CSF/IL-3 fusions, or other cytokines such as TNF-alpha or c-kit ligand.

Cytokines such as IL-12 amplify the antigen presenting and immunomodulatory capabilities of DC and inhibit tumor angiogenesis which consecutively can induce immune susceptibility of the tumor. Conversely, cytokines such as IL-7 may induce more potent T cell responses and effectively reverse T cell defects in vivo. These cytokines can be administered as soluble or microparticle encapsulated protein or by introducing the gene encoding the cytokine in viral or non-viral vectors. Systemic delivery of such cytokines along with local anti-tumor gene therapies may increase the tumor distribution of these cytokines, which may be required for long term reversal of T cell defects and effective tumor responses. These cytokines, depending on the mode of administration, may have a critical role in exploiting the immune inflammation for an efficient anti-tumor immune response.

Enhanced Combination Therapies

The present invention provides for further enhancement of the anti-tumor effect by including additional anti-tumor treatments with the ATF2 inhibitor anti-tumor therapy of the invention. For example, the present invention contemplates further combinations with tumor growth inhibitors, anti-angiogenesis treatment, tumor antigen and whole tumor vaccines, chemotherapeutic agents, radiation, and surgery (tumor resection).

Tumor growth inhibitors. The term "tumor growth inhibitor" is used herein to refer to a protein that inhibits tumor growth, such as but not limited to interferon (IFN)-gamma, tumor necrosis factor (TNF)-alpha, TNF-beta, and similar cytokines. Alternatively, a tumor growth inhibitor can be an antagonist of a tumor growth factor. Such antagonists include, but are not limited to, antagonists of tumor growth factor (TGF)-beta and IL-10. The present invention contemplates administration of tumor growth inhibitor proteins systemically, or alternatively by gene therapy.

Anti-angiogenic factors. Tumor angiogenesis is an integral part of tumor progression and a variety of therapies targeted to inhibit angiogenesis are under development as cancer therapies. Anti-angiogenesis molecules vary from anti-angiogenic proteins (e.g., angiostatin) to small molecules that block growth factor receptor mediated effects. Anti-angiogenesis therapies primarily reverse the growth/apoptosis balance of the tumor and induce dormancy. Once the administration of these therapies is halted, angiogenesis can resume and tumor growth progresses. Anti-angiogenesis is a powerful mechanism to specifically reduce the bulk of the tumor without adverse side effects in patients. The dormancy therapy induced by anti-angiogenesis paves the way for immunotherapy schemes to succeed by debulking the tumor, altering the tumor microenvironment, eliminating the immunosuppressive effects, and making the tumor more susceptible for immune mediated clearance.

An "anti-angiogenic factor" is a molecule that inhibits angiogenesis, particularly by blocking endothelial cell migration. Such factors include fragments of angiogenic proteins that are inhibitory (such as the ATF of urokinase), angiogenesis inhibitory factors, such as angiostatin and endostatin; soluble receptors of angiogenic factors, such as the urokinase receptor or FGF/VEGF receptor; molecules which block endothelial cell growth factor receptors (O'Reilly et. al. Cell 1997, 88:277-285; and O'Reilly, Nat. Med. 1996, 2:689-692), and Tie-1 or Tie-2 inhibitors. Generally, an anti-angiogenic factor for use in the invention is a protein or polypeptide, which may be encoded by a gene transfected into tumors using the vectors of the invention. For example, the vectors of the invention can be used to deliver a gene encoding an anti-angiogenic protein into a tumor in accordance with the invention. Examples of anti-angiogenic factors include, but are not limited to, the amino terminal fragment (ATF) of urokinase, containing the EGF-like domain (e.g., amino acid residues about 1 to about 135 of ATF); ATF provided as a fusion protein, e.g., with immunoglobulin or human serum albumin (PCT Publication No. WO 93/15199); angiostatin (O'Reilly et al., Cell 1994, 79:315-328); tissue inhibition of metalloproteinase (Johnson et al., J. Cell. Physiol. 1994, 160:194-202); or inhibitors of FGF or VEGF such as soluble forms of receptors for angiogenic factors, including but not limited to soluble VGF/VEGF receptor, and soluble urokinase receptor (Wilhem et al., FEBS Letters 1994, 337:131-134). The present invention contemplates administration of anti-angiogenesis factors systemically, or alternatively by gene therapy.

Vaccines. In order to increase the tumor antigen specific immune response, one could introduce defined tumor associated antigens (TAA) in the system to specifically increase the level of antigen. These TAA could be introduced as proteins, peptides or as genes in any viral or non-viral expression vectors. Immunization with these antigens could either follow or occur during anti-tumor therapy schemes. Essentially, this strategy enhances an effective immune response against specific antigen in conjunction with overall immune response. Specific immunization may lead to the expression of an immune enhancing cytokine, milieu which can promote the response against the antigens released by the tumor necrosis. Such immunization could be combined with immune activating cytokines (protein or genes) to further enhance the effects.

Besides the defined antigen based vaccines, a number of vaccine strategies are being explored in the laboratory as well as in the clinic. One well researched strategy in animal models is the modification of autologous or allogeneic tumor cell using cytokine genes (e.g., IL-2, GM-CSF, IL-12, IL-4) as well as some key costimulatory molecule genes (e.g., B7.1, B7.2). These gene modified tumor vaccines prove the concept of breaking peripheral tolerance and anergy using immunological mechanisms (Clary et al. Cancer Gene Ther. 1997, 4:97-104; and Gilboa, Semin. Oncol. 1996, 23:101-107). Other similar approaches include use of tumor lysates, proteins, or RNA pulsed DC and fusion of tumor cells with DC to induce a potent tumor immune response. All these approaches have a common theme, which is the delivery of antigenic molecules to the DC to induce efficient processing and presentation of these antigens to T cells.

Screening and Chemistry

The recombinant cells of the invention that express a reporter gene under control of an ATF2-regulated expression control sequence, provide for development of screening assays, particularly for high throughput screening of molecules that up- or down-regulate the activity of the reporter gene expressed under the control of ATF2. Accordingly, the present invention contemplates methods for identifying specific antagonists and agonists of ATF2 that modulate its ability to regulate transcription using various screening assays known in the art. Such agonists and antagonists ("modulators") are referred to herein as "compounds". Compounds can be lead compounds for further development, or therapeutic candidates for pre-clinical and clinical testing.

Any screening technique known in the art can be used to screen for agonists or antagonists. The present invention contemplates screens for small molecules and mimics, as well as screens for natural products that bind to and agonize or antagonize ATF2-mediated transcription in vivo. For example, natural products libraries can be screened using assays of the invention for molecules that agonize or antagonize ATF2 transcription.

Knowledge of the primary sequence of the ATF2 inhibitory polypeptide fragment, and the similarity of that sequence with proteins of known function, can provide an initial clue as inhibitors or antagonists. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 1990, 249:386-390; Cwirla, et al., Proc. Natl. Acad. Sci. USA 1990, 87:6378-6382; and Devlin et al., Science 1990, 49:404-406), very large libraries can be constructed ($10^6$-$10^8$ chemical entities). A second approach uses primarily chemical methods, of which the Geysen method (Geysen et al., Molecular Immunology 1986, 23:709-715; and Geysen et al. J. Immunologic Methods 1987, 102:259-274; and the method of Fodor et al. (Science 1991, 251:767-773) are examples. Furka et al. (14th International Congress of Biochemistry 1988, Volume #5, Abstract FR:013; Furka, Int. J. Peptide Protein Res. 1991, 37:487-493), Houghton (U.S. Pat. No. 4,631,211) and Rutter et al. (U.S. Pat. No. 5,010,175) describe methods to produce a mixture of peptides that can be tested as agonists or antagonists.

In another aspect, synthetic libraries (Needels et al., Proc. Natl. Acad. Sci. USA 1993, 90:10700-4; Ohlmeyer et al., Proc. Natl. Acad. Sci. USA 1993, 90:10922-10926; Lam et al., PCT Publication No. WO 92/00252; and Kocis et al., PCT Publication No. WO 9428028) and the like can be used to screen for compounds according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co.® (Trevillet, Cornwall, UK), Comgenex® (Princeton, N.J.), Brandon Associates (Merrimack, N.H.), and Microsource® (New Milford, Conn.). A rare chemical library is available from Aldrich® (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996, 14:60).

In Vitro Screening Methods

According to the present invention, a recombinant ATF2-reporter gene promoter activity system is constructed. Candidate agents are added to in vitro cell cultures of host cells, prepared by known methods in the art, and the activity of the reporter gene is measured. Various in vitro systems can be used to analyze the effects of a new compound on reporter gene expression under control of ATF2. Preferably, each experiment is performed in triplicate at multiple different dilutions of compound.

Reporter genes for use in the invention encode detectable proteins, include, but are by no means limited to, chloramphenicol transferase (CAT), □-galactosidase (□-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

GFP has been modified to produce proteins that remain functional but have different fluorescent properties. Heim et al (U.S. Pat. No. 5,625,048) modified GFP resulting in amino-acid changes which exhibited different excitation and emission spectra with visibly distinct colors and increased intensities of emission. Bjorn et al. (PCT Publication No. WO 96/23898) developed a new construct which encoded a modified GFP but also contained an enzyme recognition site. Bjorn et al (PCT Publication No. WO 97/11094) also developed new fluorescent proteins with increased intensity compared to the parent proteins. Hauswirth et al (PCT Publication No. WO 97/26633) developed a GFP protein optimized to provide higher levels of expression in mammalian cells. Gaitanaris et al. (PCT Publication No. WO 97/42320) modified GFP resulting to increase the intensity of fluorescence, e.g., by some twenty times greater than wild-type GFP, therefore increasing the sensitivity of detection. Cubitt et al. (PCT Publication No. WO 98/06737) developed modified GFP which could be easily distinguished from the already known green and blue fluorescent proteins. Evans et al. (PCT Publication No. WO 98/21355) developed new GFP mutants excitable with blue and white light.

The host cell screening system of the invention permits two kinds of assays: direct activation assays (agonist screen) and inhibition assays (antagonist screen). An agonist screen involves detecting changes in the level of expression of the reporter gene by the host cell contacted with a test compound; generally, reporter gene expression increases. If the reporter gene is expressed, the test compound has not affected ATF2 transcription activity; if the reporter gene expression increases, the test compound is a candidate for developing an ATF2 activator drug for use in conditions where inhibition of apoptosis is desirable.

An antagonist screen involves detecting expression of the reporter gene by the host cell when contacted with a test compound. If there is no change in expression of the reporter gene, the test compound is not an effective antagonist. If reporter gene expression is reduced or eliminated, the test compound has inhibited ATF2-mediated gene expression, and is thus a candidate for development of a cancer therapeutic.

The reporter gene assay system described here may be used in a high-throughput primary screen for agonists and antagonists, or it may be used as a secondary functional screen for candidate compounds identified by a different primary screen, e.g., a binding assay screen that identifies compounds that modulate ATF2 transcription activity.

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable. The use of high-throughput screening assays to test for agents is greatly facilitated by the availability of large amounts of purified polypeptides, as provided by the invention.

In Vivo Screening Methods

Intact cells or whole animals expressing a gene encoding ATF2 can be used in screening methods to identify candidate drugs.

In one series of embodiments, a permanent cell line is established. Alternatively, cells are transiently programmed to express an ATF2 gene by introduction of appropriate DNA or mRNA, e.g., using the vector systems described above. In still another embodiment, cells (such as human tumor cells) that express ATF2 endogenously can be sued. Identification of candidate compounds can be achieved using any suitable assay, including without limitation (i) assays that measure selective binding of test compounds to ATF2 (ii) assays that measure the ability of a test compound to modify (i.e., inhibit or enhance) a measurable activity or function of ATF2 and (iii) assays that measure the ability of a compound to modify (i.e., inhibit or enhance) the transcriptional activity of sequences derived from the promoter (i.e., regulatory) regions the ATF2 gene.

EXAMPLES

The present invention will be better understood by reference to the following Examples, which are provided by way of exemplification and not by way of limitation.

Example 1

ATF2-derived Peptides Alter Resistance of Human Tumor Cell Lines to UV-irradiation and Chemical Treatment This Example aims at assessing the ability to sensitize melanoma cells to apoptosis by outcompeting endogenous ATF2 expression with ATF2-derived peptide(s) alone and in combination with inhibition of p38 activities via its pharmacological inhibitor. We demonstrate that expression of a 50 amino acid residue peptide derived from the amino terminal domain of ATF2 is sufficient to sensitize melanoma as well as breast cancer cells to radiation and chemical treatment, and that the combination of this peptide with the pharmacological inhibitor of p38 is sufficient to induce programmed cell death in late-stage melanoma cells that utilizes Fas as major death signaling cascade.

Materials and Methods

Cell lines. LU1205 cells (also known as 1205LU), a late-stage human melanoma cell line, were maintained in MCDB130/L15 medium (4:1) supplemented with 5% fetal bovine serum, L-glutamine and antibiotics. LU1205 cells that stably express ATF2-derived peptide II or peptide IV were maintained in the same medium supplemented with G418 (200 mg/ml). The late-stage melanoma cells, FEMX (Ivanov et al., J. Biol. Chem. 1999, 274:14079-14089; and Ivanov et al., Oncogene 2000, 19:3003-3012) were maintained in RPMI supplemented with 10% FBS and antibiotics. The medium for WM1552 cells, an early-phase human melanoma cell line, was the same as for the cells (Ivanov et al., Oncogene 2000, 19:933-942), supplemented with insulin (5 mg/ml). Human melanocytes (FOM71; Kath et al., Anticancer Res. 1989, 9:865-872) were maintained in MCDB153 (Sigma) medium supplemented with 2% FBS (Cansera), 10% chelated FBS (Sigma), 2 mM L-glutamine (Cellgro®), 20 pM cholera toxin (Sigma), 100 nM endothelin 3 (Peninsula), 10 ng/ml stem cell factor (Research & Development) and 250 pM basic fibroblast growth factor (GIBCO®).

Chemicals. The pharmacological inhibitors of JAKs (AG490), p38 (SB203580) and PI3K (LY294002) were purchased (Calbiochem®). Mitomycin C (MMC), Adriamycin® and verapamil were purchased from Sigma. The radiomimetic drug neocarzinostatin (NCS) was obtained from Kayaku Co. (Tokyo, Japan). The nuclear export inhibitor Leptomycin B was kind gift of Dr. Yoshida (Kyushu University, Japan) (Kudo et al., Proc. Natl. Acad. Sci. USA 1999, 96:9112-9117). The chemotherapeutic drug 7-hydroxystaurosporine (UCN-01) was kindly provided by the Drug Synthesis and Chemistry Branch at NCI (Gescher, Crit. Rev. Oncol. Hematol. 2000, 34:127-135).

Stable transfection and selection. Oligonucleotides corresponding to ATF2 peptides within amino acid residue 1-50 (peptide I), 50-100 (peptide II), 100-150 (peptide III) and 150-200 (peptide IV) were PCR amplified and cloned into BamHI and XbaI sites of pcDNA3 (Invitrogen®, Carlsbad, Calif.), which contains HA-penetratin tag on its NH2-terminal domain. Cloned material was verified via sequencing. pcDNA3-HA-neo or pcDNA3-HA encoding each of the four peptides was electroporated (230V, 1050 microfarads) into the respective cell lines as previously described (Ronai, Z., et al., Oncogene 1998; 16:523-531). Cells were maintained in G418 (500 µg/ml) for 2 weeks before mixed population were pooled and characterized.

Immunohistochemistry and Western blot analysis. Cells were grown on cover slips before subjected to fixation (3% paraformaldehyde, 2% sucrose in PBS for 10 min at room temperature) followed by permealization (0.5% Triton X-100, 3 mM $MgCl_2$, 6% sucrose in PBS for 5 min on ice). Cells were than incubated with antibodies against HA-tag (5 mg/ml) for 1 h at 20° C., before washed with PBS and incubated with secondary (anti-mouse IgG) antibody that is conjugated to FITC (Roche® Chemicals) for 1 h at 20° C. Immunofluorescence analysis was carried out using a fluorescence microscope (Nikon®). Western analysis for the expression of the low molecular weight peptides was carried out using 15% Tricine-SDS-PAGE and antibodies to HA. Secondary antibodies used in this reaction were goat anti mouse IgG conjugated to horseradish peroxidase (1/500). Signals were detected using the ECL system (Amersham-Pharmacia Biotech).

Treatment and apoptosis studies of stably transfected melanoma cells. Cells were exposed to UVC at 75 $J/m^2$ as previously described (Ronai, Z., et al., Oncogene 1998; 16:523-531). SB203580 (1-10 µM) (Calbiochem®, San Diego, Calif.), NCS (50-100 ng/ml) and mitomycin C (MMC) (0.2-1 µM) were used to treat melanoma cells. Flow cytometric analysis was performed on a FACSCalibur™ flow cytometer (Becton Dickinson) using CellQuest™ software as described previously (Nicoletti et al., J. Immunol. Methods 1991; 139:271-279). Cells were pelleted and resuspended in 0.5 ml of hypotonic buffer with 0.1% Triton X-100 containing PI (40 µg/ml) and DNase-free RNase A (1 mg/ml). Cells were incubated at 37° C. for 30 min and analyzed on a FACSCalibur™ flow cytometer (Becton Dickinson). The percentage of cells to the left of the diploid G0/1 peak, characteristic of hypodiploid cells that have lost DNA, was defined as the percentage of apoptotic cells. Analysis was performed with light scatter gating. Surface expression of Fas was determined using anti-Fas-PE antibody (PharMingen® CA) and flow cytometric analysis. Cell surface expression is measured as mean fluorescence intensity (MFI).

Radiation resistance. Cells (500 or 1500 per well) were plated in triplicates on 6 well plates, 24 h before treatment (Ronai et al., Oncogene 1998; 16:523-531). In all cases, plating efficiency was pre-determined so that number of cell plated was normalized respectively. Colonies (greater than 50 cells per clone) were stained with crystal violet solution (3% in 10% methanol and PBS), 14 days After treatment. % of CFE in each treatment group was calculated based on total CFE formed in the respective controls (100%).

Results

Expression of ATF2-driven peptides in melanoma cells. The four peptides selected for the analysis span the first 200 amino acids of ATF2. We focused on this domain, which represents the trans-activating domain, since a form of ATF2 that lacked this region, efficiently decreased melanoma's resistance to radiation treatment (Ronai, Z., et al., Oncogene 1998; 16:523-531). We thus hypothesized that expression of a peptide from the transactivating domain may efficiently out-compete some of the ATF2 modifications required for its transcriptional activities. Among important sites within the first 200 amino acids are the phosphoacceptor sites for p38 and JNK (amino acid residues 69 and 71) (Gupta et al., Science 1995; 267:389-393) and the region required for ATF2 intra-molecular inhibition (within amino acid residues 150-200) (Fuchs, S. Y., et al., Mol. Cell. Biol. 1999; 19:3289-3298).

Clones of the FEMX and LU1205 melanoma cells expressing the respective peptides were selected and maintained in G418 as mixed populations. To verify expression of the peptides, mRNA was used for the RT-PCR reaction using primers against each of the corresponding peptides. PCR reactions confirmed the expression of the respective peptides. To determine expression at the protein level, immunohistochemistry was carried out using antibodies to the HA-tag. Expression of peptide II or peptide IV was clearly observed, albeit primarily in the cytoplasm. Over 80% of cells were found to express this peptide. To determine whether the peptides could also be found in the nuclear fraction, cells were treated with the nuclear export inhibitor, leptomycin B, which enabled detection of the peptide in the nuclei. Western blot analysis using antibodies directed to the HA-tag further confirmed their expression. These results demonstrate that the melanoma cells express the ATF2-derived HA-tagged peptides in both the nuclear and the cytoplasmic cellular compartments. Since these peptides were driven from ATF2 transactivating domain we have monitored possible changes to ATF2 expression and phosphorylation in cells that constitutively express these peptides. Melanoma cells that express peptide II exhibit higher degree of ATF2 phosphorylation under non-stressed growth conditions but not After exposure to UV-irradiation. Conversely, peptide IV expressing cells exhibited a higher degree of increase in ATF2 phosphorylation After UV-treatment, when compared with the parent (control vector expressing) cells. These observations suggest that expression of peptide IV, but not peptide II, may further induce the transcriptional activities of endogenous ATF2.

Figure 1B:
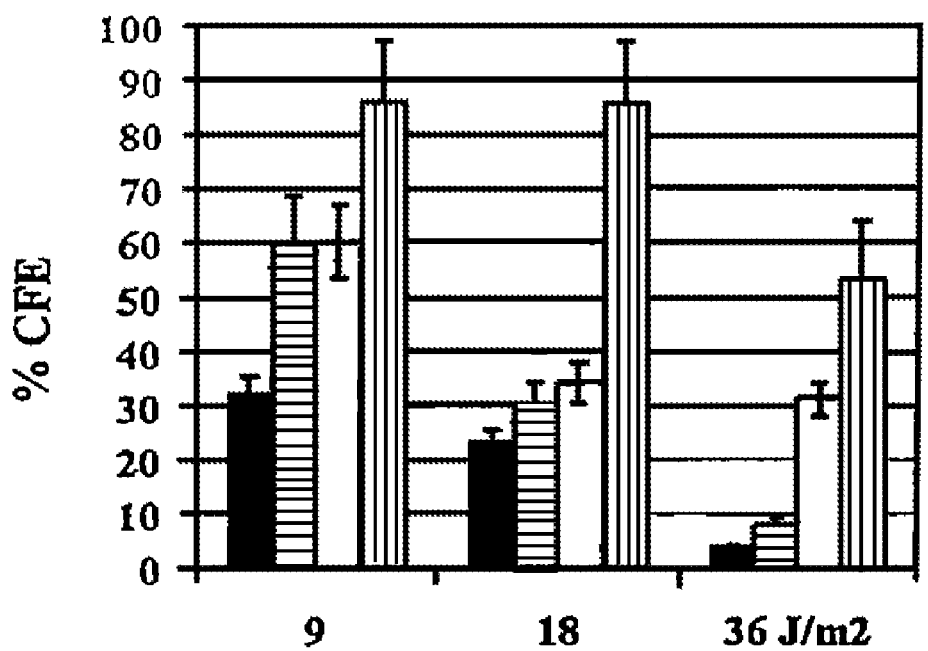

Effect of ATF2 peptides on radiation resistance of human melanoma cells. To determine the effect of each of the four peptides on the radiation resistance of the LU1205 and FEMX, two late phase melanoma derived cell lines which were selected based on their high resistance to radiation, we used the classical radiation resistance assay, namely, colony-forming efficiency. Cells plated to assure equal numbers were subjected to irradiation using UV-C as a source. Colonies numbering more than 50 cells per clone were counted 14 days later. These analyses, carried out in triplicate, revealed that two of the four peptides induced clear changes in the sensitivity of melanoma cell lines to UV-treatment. Whereas the expression of peptide IV led to an increase in resistance to UV-irradiation, peptide II sensitized both LU1205 and FEMX melanoma cells to UV-treatment (FIG. 1). Peptide II caused up to a 3-fold decrease in the % of CFE of LU1205 cells and brought about an up to 10 fold decrease in % of CFE of the FEMX cells (FIG. 1A). Peptide IV caused up to a 2.5-fold increase in the % of CFE of both LU1205 and FEMX melanoma cell line in response to UV-treatment (FIG. 1B). These observations suggest that peptide II efficiently decreased the resistance of melanoma cells to irradiation, whereas peptide IV had the opposite effect. Since these two peptides exhibited the most pronounced effects, they were selected for additional characterization.

Figure 2A:
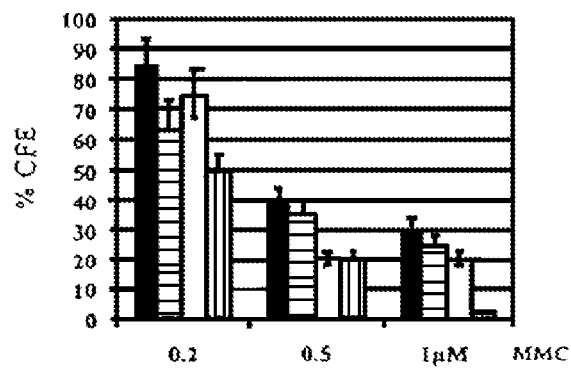
FIGS. 2A, 2B, 2C, and 2D. ATF2-peptides alter resistance of melanoma cells to mitomycin C, NCS and Adriamycin® with or without verapamil. LU1205 and FEMX cells expressing control empty vector (first and third bars in each set) or peptide (second and fourth bars in each set), either peptide II (FIG. 2A) or peptide IV (FIG. 2B), were treated with mitomycin C (MMC) at the indicated concentrations and CFE were analyzed 14 days later.
Figure 2B:
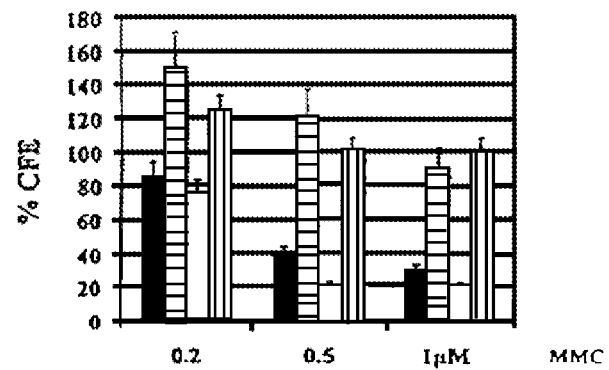

Effect of ATF2 peptides on melanoma's resistance to chemical treatment. To determine whether the effect of ATF2-driven peptides is not limited to UV-irradiation, we subjected the melanoma cells to treatment with chemicals often used for chemotherapy. Treatment of FEMX cells that express peptide II with 1 □M MMC revealed up to a 10-fold decrease in the fraction of CFE when compared with the control FEMX neo expressing cells (FIG. 2A; 1 □M dose). Peptide II has much less pronounced effects on the sensitivity of LU1205 to MMC. Conversely, peptide IV was as efficient in increasing (4- to 5-fold) the resistance of both melanoma cell lines to MMC treatment (FIG. 2B). These results suggest that ATF2-driven peptides could also alter the sensitivity of selective melanoma cells to MMC.

Figure 2C:
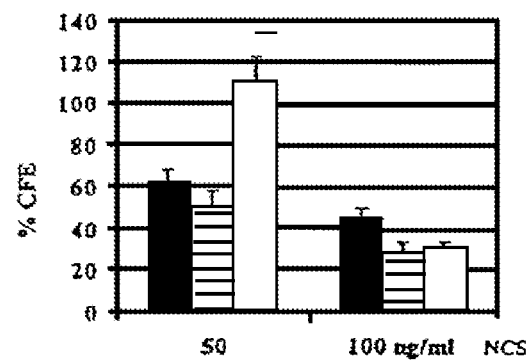

Treatment with the chemical NCS, which mimics the effects of X-radiation, did not reveal substantial differences in the sensitivity of melanoma cells expressing ATF2-driven peptide II (FIG. 2C). Peptide IV exhibited close to a 2-fold increase in the resistance to low dose of NCS (FIG. 2C). These results suggest that ATF2 peptides are not effective in sensitizing melanoma cells to the radiomimetic drug NCS. Indeed, ATF2-peptides expressing melanoma cells did not exhibit changes in the sensitivity to X-ray treatment, suggesting that a different signaling pathway is utilized by melanoma to acquire resistance to X-radiation.

Figure 2D:
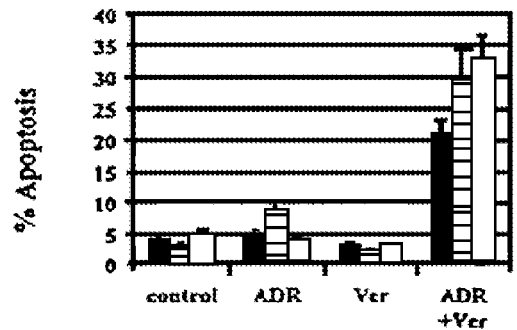

Control and peptide expressing cultures were also subjected to treatment with commonly used chemotherapeutic drug Adriamycin® alone or in combination with verapamil, which is used to avoid induction of drug resistance. As shown in FIG. 2D, sensitivity of LU1205 cells to Adriamycin® induced programmed cell death increased in response to Adriamycin® treatment (2-fold when compared with control). Combination of Adriamycin® and verapamil caused 4-fold increase in apoptosis of control cells, and an additional (50%) increase in peptide II expressing cells (10-fold increase comparable to neo expressing cells). Peptide IV expressing LU1205 cells exhibited a 70% increase in degree of apoptosis over the control neo expressing cells subjected to the combination of Adriamycin® and verapamil (FIG. 2D). These observations suggest that the effects mediated by ATF2-peptides are selective to the form of DNA damage and stress.

Figure 3A:
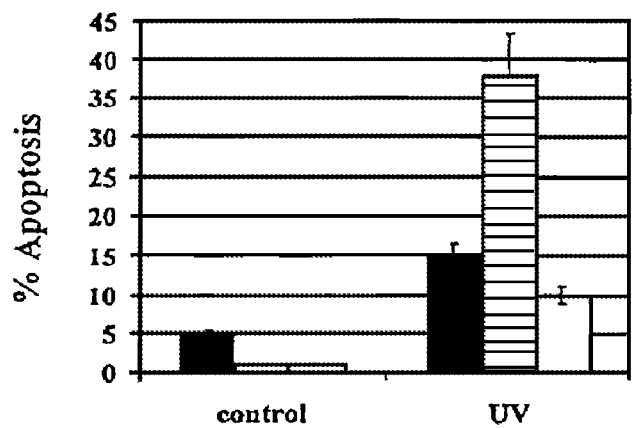
FIGS. 3A, 3B, and 3C. ATF2-peptides alter sensitivity of melanoma cells to UV-induced apoptosis. The late-stage melanoma cell lines LU1205 (FIG. 3A) and FEMX (FIG. 3B), and the early-phase melanoma cell line WM1552 (FIG. 3C) which stably express the respective peptides (peptide II, second bars or peptide IV, third bars), or control (neo/empty vector; first, solid, bars) were subjected to the indicated doses of UV-C (75 J/m2), and degree of apoptosis was monitored 36 h later as indicated in Methods. Data shown is representative of 3 independent experiments.
Figure 3B:
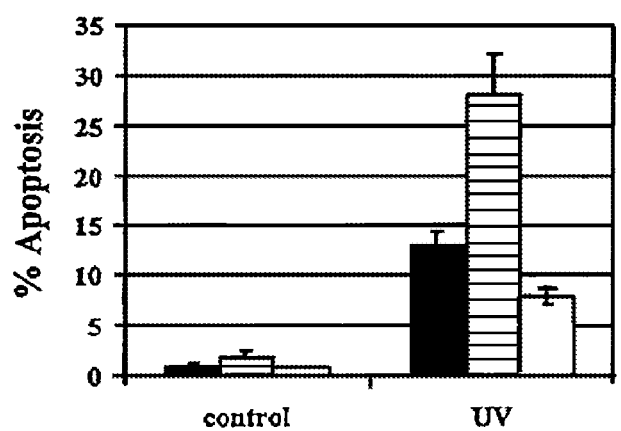

ATF2-peptides affect UV-induced apoptosis of human melanoma cells. Previous studies showed the mechanism underlying ATF2's ability to alter melanoma's resistance to radiation to involve change in the melanoma cell's ability to undergo programmed cell death (Ronai, Z., et al., Oncogene 1998; 16:523-531). For this reason we determined whether the ATF2-driven peptides are capable of altering the melanoma cell's sensitivity to apoptosis. FACS analysis of the melanoma cells carried out 36 h After irradiation clearly revealed change in the percentage of cells that had undergone programmed cell death. Peptide II caused an increase (from 15% to 38%) in the apoptotic fraction of UV-treated LU1205 cells (FIG. 3A), and a corresponding increase (from 13% to 28%) was seen in UV-treated FEMX cells that expressed this peptide (FIG. 3B). Conversely, peptide IV decreased the fraction of cells that underwent apoptosis, both in LU1205 cells (from 15% to 10%; FIG. 3A) and similarly in FEMX cells (from 13 to 8%; FIG. 3B). These observations suggest that the changes in resistance to irradiation caused by the two peptides are mediated by alterations in the melanoma cells' sensitivity to apoptosis in response to UV-irradiation.

Figure 3C:
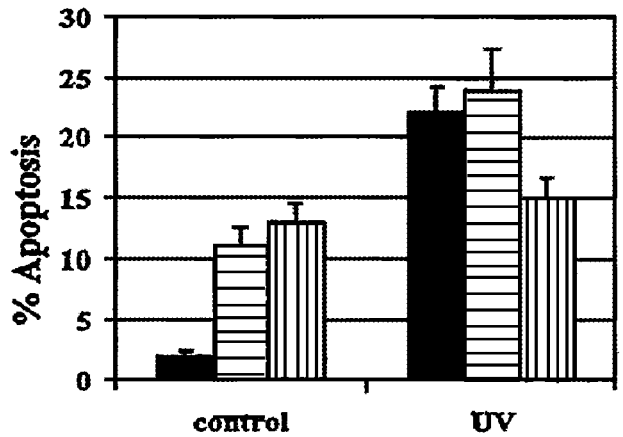

We also assessed the effect of ATF2-driven peptides on UV-induced apoptosis in the early-phase WM1552 melanoma cell line. Previous studies had disclosed that WM1552 early-phase melanoma cells are more sensitive to irradiation when compared with late-stage melanoma cells as a result of impaired signaling by TRAF2/GCK, which affects the activities of both the JNK and the NF-kB pathways (Ivanov, V. N., et al., Oncogene 2000; 19:933-942). In contrast to its effects on the LU1205 and FEMX late-stage melanoma cells, peptide II no longer was able to elicit sensitization of these cells to UV effects (compare control and peptide expressing WM1552 cells in FIG. 3C). Nevertheless, both peptides caused a noticeable (4- to 5-fold) increase in the basal level of apoptosis of these early-phase melanoma cells (FIG. 3C). These results imply that peptide II's ability to increase melanoma cells' sensitivity to irradiation may depend on the nature of stress signaling cascade which is different in the early-phase melanoma cells (weak JNK and NF-kB activities when compared with the late stage LU1205; (Ivanov, V. N., et al., Oncogene 2000; 19:933-942). UV-treatment of peptide IV expressing WM1552 cells did not cause higher level of apoptosis when compared to non-treated WM1552 cells expressing this peptide (FIG. 3C), suggesting that expression of this peptide attenuated UV ability to induce cell death.

ATF2-peptides alter sensitivity to UV radiation in non-melanoma tumor-derived cell lines. An important consideration in our analysis of ATF2-driven peptides was to determine whether similar effects could be elicited in non-melanoma tumors. To this end different tumor-derived cell lines were transfected with peptide II or peptide IV, and stably expressing cells were then used for analysis.

Figure 4A:
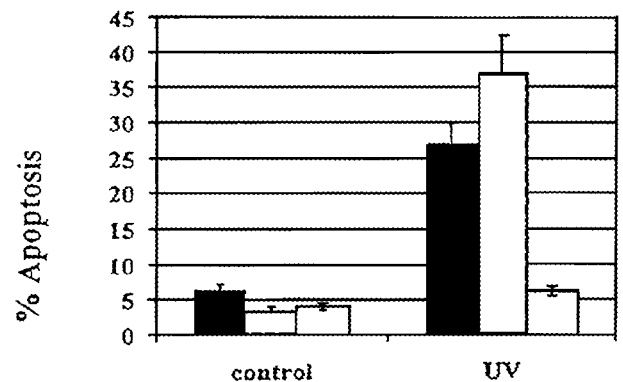
FIGS. 4A, 4B, and 4C. Expression of ATF2-derived peptides sensitizes breast cancer cells to UV-treatment. MCF7 (FIG. 4A), MCF7 resistant to Adriamycin® (MCF-ADR, FIG. 3B) or 293T cells (FIG. 4C) were subjected to UV-irradiation at the indicated doses. Degree of apoptosis was measured 36 h later as indicated in Methods. In each set of bars, the first (solid) bars are for cells that express neo; the second (striped) bars are for cells that express peptide II, and the third (open) bars are for cells that express peptide IV.

Expression of peptide II in the MCF7 breast cancer-derived cell line caused a minimal effect on the basal level of apoptosis. Nevertheless, whereas neo-resistant parent MCF7 cells (used as a control) exhibited a 4-fold increase in apoptosis following UV-treatment, the peptide II-expressing cells exhibited a close to 9-fold increase in degree of apoptosis relative to non-irradiated cells (FIG. 4A). Opposite to the effect of peptide II, peptide IV caused a decrease in the degree of apoptosis After UV-treatment (5-fold when compared with MCF7 neo control cells; FIG. 4A). These findings establish that ATF2-driven peptides are also capable of altering the sensitivity of breast cancer cells to UV-treatment as they are in late-stage melanoma cell lines.

Figure 4B:
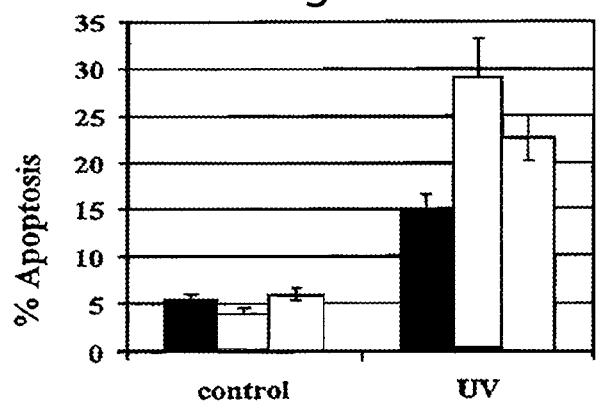

MCF7 is among the better-characterized breast cancer cell lines. The latter resulted in a battery of MCF7-derivatives that were selected for growth based on their ability to develop drug resistance. One such MCF7-derivative is the Adriamycin®-resistant MCF7 cell line (MCF7-Adr), which is 1000 times more resistant to Adriamycin® than the original cells line. Peptide II-expressing MCF7-Adr cells exhibited an 8-fold increase in apoptosis following UV-treatment as compared with the 3-fold increase in the MCF7-Adr-neo controls (FIG. 4B). This result suggests that peptide II retained its ability to sensitize cells to UV-treatment even if they have acquired resistance to chemotherapeutic drugs. Peptide IV was no longer able to increase the resistance of the cells, as seen in all other cases, but rather sensitized them (from less than 3-fold in controls to greater than 4-fold in MCF7-Adr cells expressing peptide IV). That Adriamycin® resistance attenuates peptide IV's ability to elevate resistance of MCF7 cells to UV-treatment implies that Adriamycin® and peptide IV may utilize similar cellular pathways required to increase resistance of tumor cells to radiation and chemical treatments. Since they are required to acquire chemotherapeutic resistance, these pathways are no longer affected by peptide IV. The basal degree of apoptosis, which was affected in the MCF7 cells by both ATF2-driven peptides (FIG. 4A), was no longer seen in the MCF-Adr cells (FIG. 4B), further pointing to changes in MCF7-Adr that impaired the contribution of the ATF2 pathway to basal degree of programmed cell death.

Figure 4C:
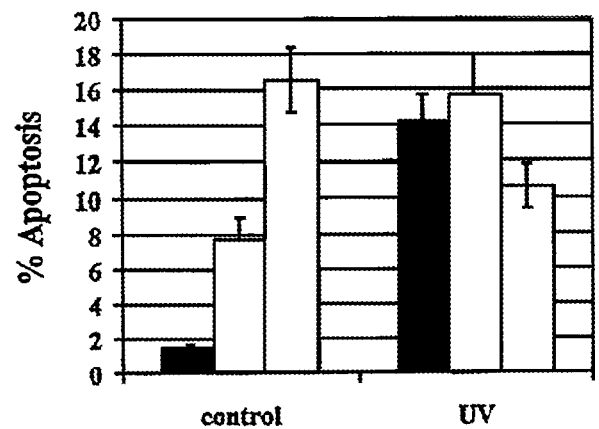

Unlike its effect in the breast cancer derived cell lines, peptide II was not able to increase the sensitivity of in vitro transformed 293T human kidney embryonic cells to irradiation. Nevertheless, as also seen with MCF7 and WM1552 cells, both peptides were able to efficiently increase the basal degree of apoptosis. Whereas peptide II caused a 5-fold increase, peptide IV led to a 15-fold increase in the degree of basal apoptosis seen in 293T cells that were maintained under normal growth conditions (FIG. 4C). Further, peptide IV efficiently increased the basal degree of apoptosis in non-stressed cells.

ATF2-peptides increase sensitivity of melanoma tumor-derived cell lines to chemotherapeutic drug UNC01. To further explore the possible sensitization of melanoma cells to apoptosis by relevant chemotherapeutic drugs, we chose to test the effect of UCN-01. UCN-01 is a protein kinase inhibitor currently undergoing clinical trials for cancer treatment, which abrogates G(2) checkpoint function via targeting the Chk1 kinase and the Cdc25C pathway, and sensitizes p53-defective cancer cells to DNA-damaging agents (Graves P R, et al., J Biol Chem 2000; 275:5600; Mack P C, et al., Clin Cancer Res. 1999; 259:6-604; Yu L, et al., J Biol. Chem. 1998; 273:33455-64; and Gescher A, Crit. Rev Oncol Hematol. 2000; 34:127-35). 30% of LU1205 cells underwent apoptosis in response to a 1 □M dose of UCN-01. Expression of peptide II further increased fraction of cells undergoing apoptosis to 40%, whereas expression of peptide IV somewhat decreased the degree of cell death (to 21%). Higher dose of UCN-01 caused up to 48% apoptosis in peptide II expressing LU1205 cells, when compared with the 36% seen in the parent cells. A substantial greater sensitization was seen in the FEMX cells. Over a 3-fold increase in the degree of UCN-01-elicited apoptosis was seen in FEMX cells that express peptide II (from 10 to 36% at the 1 mM dose, and from 18 to 54% at the 5 mM dose), and to a lesser extant in FEMX cells that express peptide IV. These results suggest that peptide II is capable of sensitizing melanoma cells to the chemotherapeutic drug UCN-01 and that the degree of sensitization varies among the different melanoma tumor derived cells.

Further assessment of sensitization to UCN-01 was carried out in the breast cancer cell line MCF7. MCF7 cells that express peptide II exhibit a close to 2-fold increase in their sensitivity to UCN-01 elicited apoptosis. This increase was dose-dependent, as higher dose of UCN-01 further sensitized peptide II and to a lower degree, peptide IV-expressing MCF7 cells to apoptosis.

Together, these finding establish that the expression of ATF2 peptides and in particular peptide II efficiently sensitizes melanoma and breast cancer cells to apoptosis induced by chemotherapeutic drugs, including MMC, Adriamycin®+verapamil and UCN-01.

ATF2-driven peptides increase Fas expression. Our previous studies revealed that Fas is the primary apoptotic pathway in late-stage melanoma cells, which is balanced by the relative expression levels of TNF□(Ivanov, V. N., et al., J. Biol. Chem. 1999; 274:14079-14089). Decrease in TNF□ or increase in Fas results in elevated sensitivity to apoptosis. To determine the possible mechanism by which peptide II is capable of increasing the sensitivity of the human melanoma cell to UV-induced apoptosis, we followed changes in the cell surface expression of Fas. FACS analysis of LU1205 cells that express peptide II revealed a noticeable increase (from mean fluorescence intensity of 122 to 186-data not shown), whereas peptide IV did not cause major changes in cell surface expression of Fas. Analysis of Fas promoter activity using the –460 Fas promoter region revealed an increase in Fas-mediated transcription in peptide II-expressing LU1205 cells, whereas peptide IV expressing LU1205 cells exhibit a decrease in Fas promoter mediated transcription. Western blot analysis demonstrates an increase in the overall level of Fas protein in peptide II expressing melanoma cells. The effects of ATF2-driven peptides on Fas expression point to the mechanism by which these peptides alter sensitivity of melanoma to UV and chemical treatments.

Figure 5A:
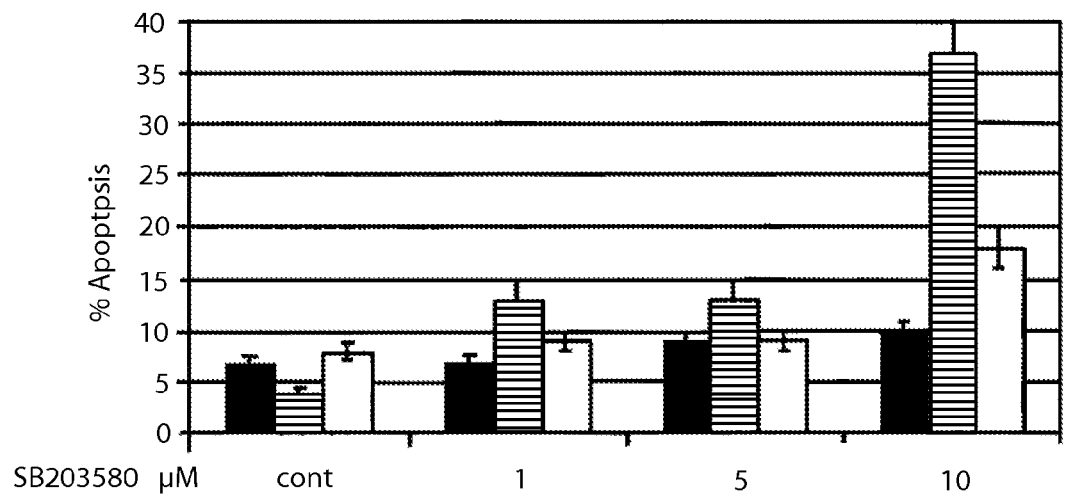
FIGS. 5A, 5B, and 5C. Expression of ATF2-derived peptides sensitizes melanoma cells to inhibitors of p38 and JAK. LU1205 cells expressing control or ATF2-derived peptides were treated with the pharmacological inhibitors of p38 (SB203580, FIG. 5A), JAKs (AG490, FIG. 5B), or PI3K (LY294002, 5B) for 6 h and degree of programmed cell death was measured 36 h later. In each set of bars in 5A and 5B, the first (solid) bar is for neo-expressing LU1205 cells, the second (striped) bar is for peptide II-expressing LU1205 cells, and the third (open) bar is for peptide IV-expressing LU1205 cells; "cont" means control.

Inhibition of p38 induces apoptosis of late-stage LU1205 melanoma cells that express peptide II. P38 signaling of death pathways appears to utilize at least two independent cascades to affect melanoma resistance to radiation. The first has been attributed to the effect of the p38 substrate, ATF2, which upregulates expression of TNF□ (Ivanov, V. N., et al., J. Biol. Chem. 1999; 274:14079-14089), whereas the second relies on p38's ability to suppress NF-kB activities, resulting in suppression of Fas transcription (Ivanov, V. N., et al., Oncogene 2000; 19:3003-3012). Given the dual activities elicited by p38, we sought to inhibit p38 catalytic activity in cells that already express ATF2-driven peptides. Treatment of the LU1205 cells expressing peptide II with SB203580, the pharmacological inhibitor of p38 (Cuenda, A., et al., FEBS Lett. 1995; 364: 229-233), resulted in a dose-dependent increase in the degree of apoptosis (FIG. 5A). Whereas low doses of p38 inhibitor were sufficient to mediate a 3-fold increase in cell death, the higher doses (10 µM), which are likely to affect other kinases as well as p38 (i.e., JNK), led to an additional increase in the degree of cell death (greater than 6-fold) in peptide II expressing melanoma cells. This result suggests that in combination with peptide II expression, inhibition of stress kinase activities is sufficient to induce apoptosis in late-stage melanoma cells. The effects of p38 inhibitor and peptide II expression were additive, further supporting the notion that two p38-independent pathways were affected. Whereas treatment of LU1205 cells that express peptide IV with low concentrations of SB203580 did not alter the degree of cell death, at a higher concentration there was a 2-fold increase in the amount of cell death (FIG. 5A). These observations suggest that peptide IV's ability to increase resistance of human melanoma cells to irradiation can be augmented by inhibition of stress kinases.

Figure 5B:
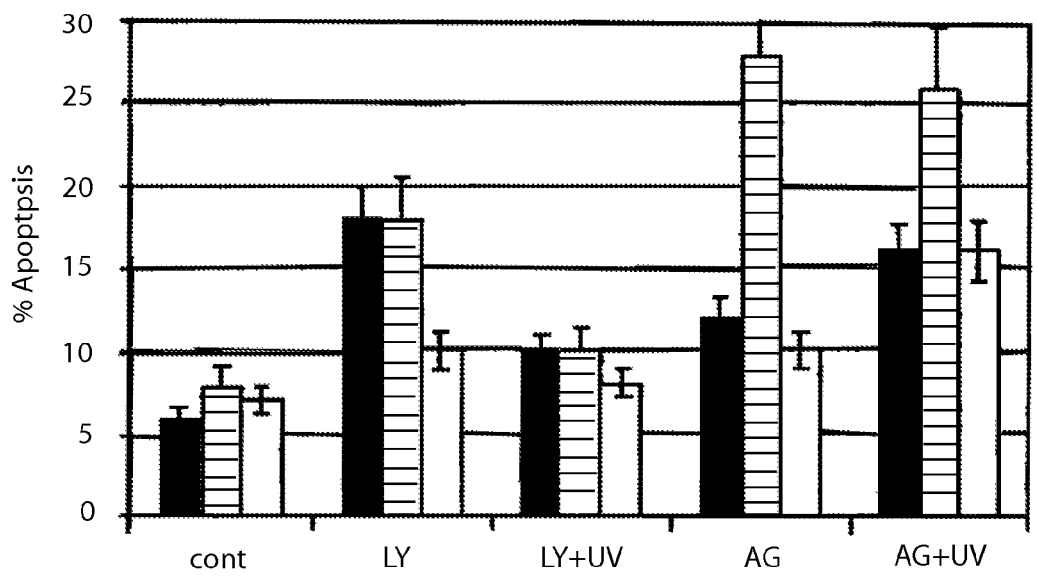

In contrast to the effect of the p38 inhibitor, treatment with inhibitor of PI3K (LY294002) did not alter sensitivity of neither parent nor ATF2-peptide expressing melanoma cells to UV-induced apoptosis (FIG. 5B). Conversely, treatment with the JAK inhibitor (AG490) led to a 3-fold increase in the sensitivity of peptide II expressing LU1205 cells to UV-induced apoptosis (FIG. 5B). This observation suggests that peptide II ability to sensitize melanoma cells to UV-treatment may also utilize members of the STAT family, which are JAK substrates.

Figure 5C:
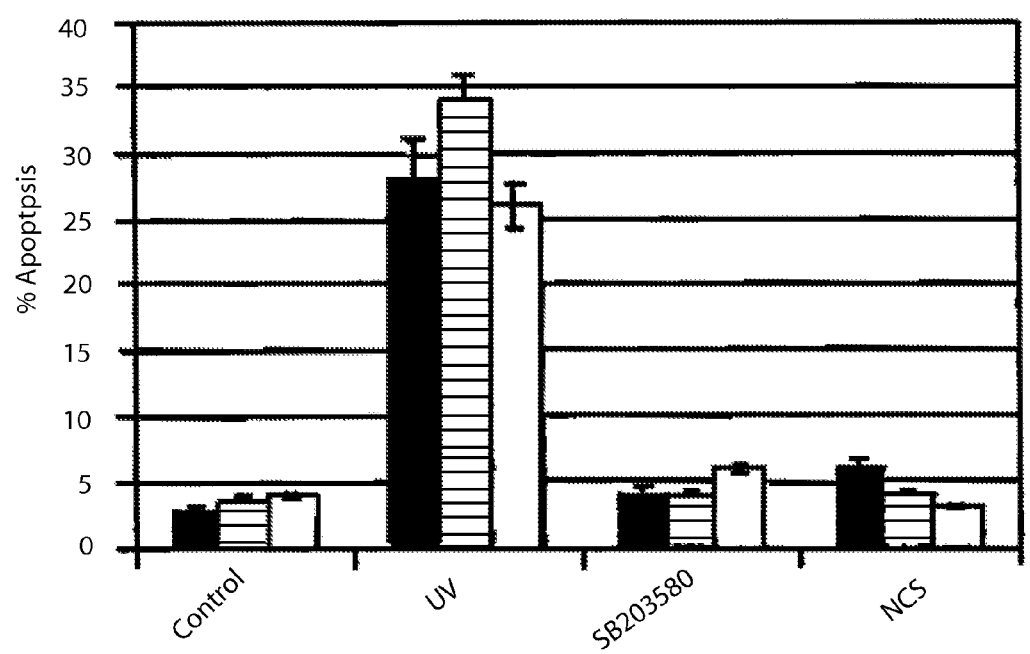

Given the differences among the early- and late-stage melanoma cells tested here, we have further characterized whether ATF2 peptides could elicit changes in the sensitivity to apoptosis of normal melanocytes. Transient expression of peptide II did not cause a significant increase in melanocytes sensitivity to undergo UV-induced apoptosis. However, unlike their effect in late-stage melanoma cells, neither NCS nor SB203580 elicited any significant changes in degree of apoptosis of these melanocytes (FIG. 5C). These observations further support the findings made with early-phase melanoma cells, which suggest that the changes elicited by ATF2 peptides are limited to the late-stage melanoma cells due to their altered stress and apoptotic signaling cascades.

SW1 mouse melanoma cells expressing peptide II are sensitized to apoptosis induced by inhibitors of stress kinases and chemotherapeutic drugs. SW1 cells expressing peptide II or control peptide were treated with the pharmacological inhibitors UCN-01, NCS, anisomycin, LY294002 (a PI3K inhibitor), PD98059 (a MAPK inhibitor), AG490 (a JAK inhibitor), and SB203580 (a p38/JAK kinase inhibitor). Twelve hours later, FACS analysis was carried out to reveal the fraction of cells smaller than G1, i.e., undergoing apoptosis. The number (percentage) or apoptotic cells was uniformly much greater in cells that express peptide II and treated with the inhibitors than with either peptide II or inhibitor alone (FIGS. 6A and 6B).

Figure 6A:
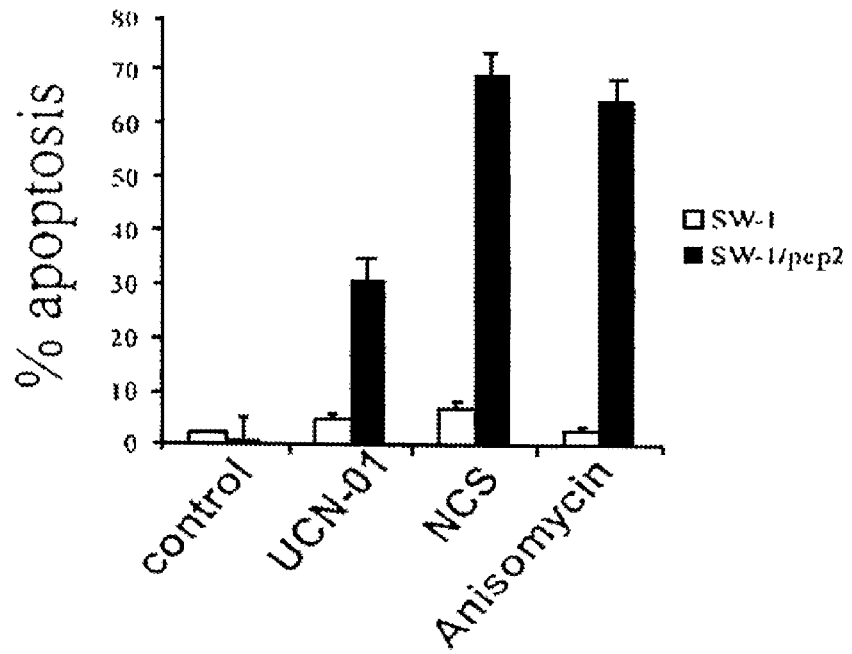
FIGS. 6A and 6B depict results of apoptosis assays using SW1 cells expressing peptide II (solid bars) or control peptide (lighter bars) and treated with the pharmacological inhibitors UCN-01, NCS, anisomycin (FIG. 6A), LY294002 (a PI3K inhibitor), PD98059 (a MAPK inhibitor), AG490 (a JAK inhibitor), and SB203580 (a p38/JAK kinase inhibitor) (FIG. 6B). Twelve hours after treatment, FACS analysis was carried out to reveal the fraction of cells smaller than G1, i.e., undergoing apoptosis.
Figure 6B:
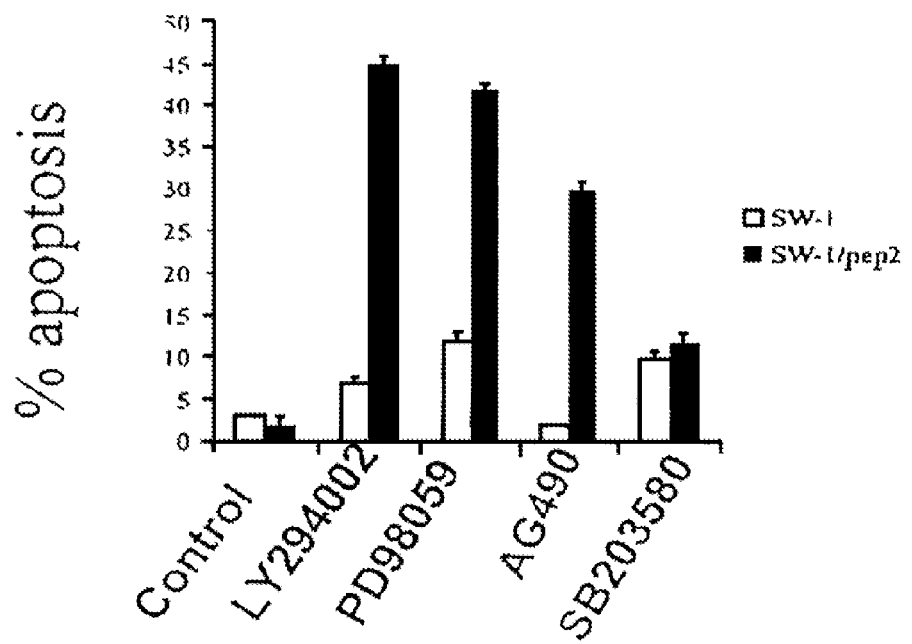

Thus, treatment of SW1 cells with chemotherapeutic, ribotoxic or radiomimetic drugs (UCN-01, NCS and anisomysin) resulted in a profound degree of apoptosis (6- to 14-fold increase) that was dependent upon the expression of the Peptide II peptide (FIG. 6A). Similarly, peptide II-expressing cells exhibited a marked increase (4-to 10-fold) in the degree of apoptosis following treatment with inhibitors of PI3K, MAPK, and JAK signaling cascades (LY204002, PD98059, AG490; and SB203580-FIG. 6B). These findings suggest that the expression of peptide II elicits changes that result in the sensitization of melanoma cells to treatment. Among the anti-apoptotic regulatory proteins, Bcl-XL was found in its cleaved form (BclXs) in melanoma cells that express the ATF2 peptide, pointing to one cellular component that may contribute to the sensitization of these melanomas to apoptosis. These data establish that cells that express a polypeptide corresponding to amino acids 50-100 of ATF2 are more prone to undergo apoptosis in response to treatment with drugs which otherwise do not affect this tumor type.

Discussion

The present study has extended earlier observations in which ATF2 was identified as an important player in the melanoma cell's ability to undergo apoptosis. Four 50 amino acid peptides obtained from the amino-terminal domain of ATF2 were tested, of which two were selected for further characterization, on the basis of their pronounced effect on late-stage melanoma cell lines. Of these two peptides, peptide II, which correspond to amino acid residues 50-100, efficiently increased sensitivity of melanoma cells to UV-irradiation as well as to chemotherapeutic, ribotoxic or radiomimetic drugs such as MMC, Adriamycin®+verapamil and UCN-01. Peptide II effects were as pronounced in the breast cancer cell line MCF7 and its derivative, MCF7-ADR, which is Adriamycin®-resistant, indicating that the effects studied here are not limited to melanoma cell lines and that peptide II may also sensitize Adr-resistant breast cancer cells to DNA damage, illustrated here via UV-treatment. Conversely, peptide II expression did not elicit changes in sensitivity to UV-induced apoptosis in 293T cells or in the early-phase WM1552 melanoma cells, nor was it effective in normal melanocytes. It is important to stress, however, that both ATF2-peptides had a pronounced effect on the basal level of apoptosis of both early melanoma (WM1552) and in vitro transformed human 293T cells, suggesting that in these cells the role of ATF2 is more important in suppression of basal—rather than in DNA damage-induced apoptosis. These differences also suggest that certain cellular components, which are shared among MCF7 and late-stage melanoma cells, are required for peptide II's ability to elicit its effects in response to DNA damage. The noticeable differences in basal as well as UV-inducible apoptosis between early- and late-stage melanoma cells are likely to be due to altered TRAF2 expression, JNK signaling and NF-κB activity, which are expected to be part of ATF2 and therefore peptide II activities.

Of interest is the finding that ATF2-peptides studied here did not alter the sensitivity of melanoma cells to X-rays or to the corresponding radiomimetic drug NCS. While the nature of cellular changes elicited by X-ray and UV-radiation are quiet different, the lack of effect on X-ray treated cells is in contrast to the effect of dominant negative or transcriptionally inactive forms of ATF2, which were also effective on X-ray resistance (Ronai, Z., et al., Oncogene 1998; 16:523-531). These differences imply that other ATF2 domains or ATF2-associated proteins are those that contribute to the resistance of the cells against X-radiation.

The mechanism by which peptide II is capable of increasing the sensitivity of tumor cells to UV irradiation and chemical treatment is likely to involve competition with the endogenous form of ATF2. Peptide II harbors amino acid residues 50-100 of the ATF2 cDNA, which contains the phosphorylation sites for the stress kinases p38 and JNK. It is possible that expression of ATF2 peptide decreases the phosphorylation of endogenous ATF2, thus rendering endogenous ATF2 inactive. Indeed, the level of ATF2 phosphorylation was reduced in UV-treated peptide II expressing melanoma cells. Along those lines, the transcriptional activities mediated by AP1 target sequences, which are regulated by the c-Jun-ATF2 heterodimers, are lower in melanoma cells that express peptide II. Earlier studies from our laboratory revealed that phosphorylation-deficient full length ATF2 has effects similar to those of the amino terminal truncated form, which serves as a dominant negative; both effectively down-regulated expression of TNF☐ (Ronai, Z., et al., Oncogene 1998; 16:523-531).

Interestingly, peptide IV, which bears amino acid residues 150-200 from the ATF2 cDNA, efficiently increased the resistance of melanoma cells to UV- and drug-induced apoptosis. Conversely, peptide IV sensitized melanoma and breast cancer cells to UCN-01 treatment, albeit, at lower efficiency than peptide II. Mechanistically, peptide IV is likely to interfere with the intramolecular inhibition of ATF2, which is mediated by intramolecular association between the C-terminus of ATF2 and the amino-terminal zinc finger region. The inhibition can be disrupted by removal of amino acid residues 150-250, which renders ATF2 constitutively active. Indeed, a naturally occurring splice form variant of ATF2 lacks amino acids 150-250 and is a constitutively active transcription factor (Georgopoulos, K., et al., Mol. Cell. Biol. 1992; 12:747-757). Interfering with the intramolecular inhibition of ATF2 is expected to result in a greater transcriptional output signal from the endogenous ATF2 protein. Indeed, peptide IV-expressing cells exhibited an elevated transcriptional output as measured via Jun-2-Luc activities.

With regard to the effect of ATF2 peptides, an intriguing observation was made with the p38 inhibitor, SB203580, which caused a marked increase in the degree of apoptosis without additional exposure to DNA damage. This important observation confirms our recent studies in which we identified an independent cellular pathway by which p38 contributes to the resistance of human melanoma to UV-induced apoptosis, namely, inhibition of NF-kB activities and as a consequence, decrease in Fas transcription (Ivanov, V. N., et al., Oncogene 2000; 19:3003-3012). Thus, the combination of ATF2 competition together with inhibition of p38 catalytic activities is sufficient to cause a marked increase in the degree of apoptosis of late-stage melanoma cells. The p38 inhibitor elicited efficient effects on human but not on mouse melanoma (FIG. 6B), probably due to altered signaling cascades that prevail in the different tumors.

The 50 amino acid residue peptide of a transcription factor also can be used as a source for rationalized drug design. Preliminary analysis of LU1205 cells that express peptide II, which were injected SC to nude mice and were subsequently subjected to SB203580 treatment revealed significant inhibition of tumor growth at the orthotopic site. Current studies are aimed at reducing the size of peptide II to a level at which it would still be capable of eliciting efficient sensitization of late-stage melanoma cells to apoptosis induced by radiation and drug treatments. If this effort is successful, small-sized peptides may then be considered as a source for pharmacomimetic drug design for treatment of melanoma.

Example 2

In Vivo Effects of Peptide II Therapy

The in vitro effects described in Example 1 were replicated in vivo in this Example. The results demonstrate that inhibition of ATF2 activity, in this case with peptide II expressed in tumor cells, alone or in combination with chemotherapeutics and p38 antagonists dramatically inhibits melanoma tumor growth, and in one instance, causes complete tumor regression. These data demonstrate that ATF2 inhibition can have a significant adjuvant effect, and in some cases direct therapeutic effect, on the treatment of tumors.

Materials and Methods

Cell lines. FEMX and LU125 cell lines were maintained and transfected as described above. SW1 and B16F10 tumor cells were maintained in DMEM supplemented with 10% FBS (Owen-Schaub et al., J. Exp. Med. 1998, 188:1717-1723) and transfected as described above.

Constructs. ATF2 peptides were cloned into HA-penetratin pcDNA3 vector as described above. For the doxycycline inducible system peptide II was cloned in frame with HA and Penetratin into SacII and XbaI sites of the PUHD10-3 vector (Gossen M., et al., Proc. Natl. Acad. Sci. USA. 1992, 89(12): 5547-51). The PeF1PrtTA vector (Gopalkrishnan R. V., et al., Nucleic Acids Res. 1999; 27(24):4775-82) places the rtTA gene under transcriptional control of the human EF-10 promoter. Replication deficient adenovirus expressing peptide II was generated by subcloning the ATF2 peptide cDNA into the corresponding adenovirus vector as previously described (Chen S. H., et al., Proc. Natl. Acad. Sci. USA 1994; 91(8): 3054-7).

Derivation of stable cell lines. Selection of clones stably expressing the rtTA construct was carried out in SW-1 cells in the presence of 600 mg/ml of G418. After the selection period 12 single colonies were picked, expanded and analyzed for activity by assaying for Luciferase activity (Gopalkrishnan R. V., et al., Nucleic Acids Res. 1999; 27(24):4775-82). The clone which exhibited 8 fold induction upon addition of Doxycycline was chosen. The positive clone, which expresses the rtTA cDNA, was contransfected with PUHDI0-3 peptide II and Pbabe Puro vectors that allow one to establish inducible expression of the respective genes (Gopalkrishnan et al., supra) and single clones were selected with 2 mg/ml of Puromycin. Positive clones were selected by Western blotting.

Treatment and apoptosis studies. Cells were exposed to concentrations of chemicals indicated in the Results. Apoptosis was assessed by quantifying the percentage of hypodiploid nuclei undergoing DNA fragmentation to the left of the diploid $G_{0/1}$ peak (Ivanov, V. N., et al., Oncogene 2000; 19:3003-3012). Surface expression of Fas was determined using anti-Fas-PE Ab (Pharmingen, Mountain View, Calif.). Flow cytometric analysis was performed on a FACSCalibur™ flow cytometer (Becton Dickinson, Franklin Lakes, N.J.) using the CellQuest™ program. When cells were subjected to treatment, chemicals were added 24 h After transfection (24-36 h prior to apoptosis analysis).

Tumor growth and metastasis evaluation in vivo. Cell lines established in culture to constitutively or inducibly express the peptide were injected into mice subcutaneously (S.C.). LU1205, FEMX and SW-1 cells that expressed control or peptide II were trypsinized, resuspended in PBS and injected SC ($1 \times 10^6$) into 6-7 week old mice in the lower flank. When the tumor reached the size of about 50 mm$^3$, 5 µM of SB203580 was injected into four areas of the LU1205 tumors every 4 days during a 2-week period. For FEMX tumors UCN-01 (2.5 mg/kg) was fed by gavage twice a day, three times per week for a total of 2 weeks. Tumor growth was monitored every two days. SW-1 cells expressing peptide II under tet-inducible vector were injected SC ($1 \times 10^6$). When tumors reached a size of about 50 mm$^3$, the mice received doxycycline in their drinking water (500 mg/ml) for a total of 2-4 weeks. At the end of the experiment, the tumors were excised and weighed. The lungs and other organs were subjected to histopathological examination to detect metastatic lesions.

Results

Figure 7A:
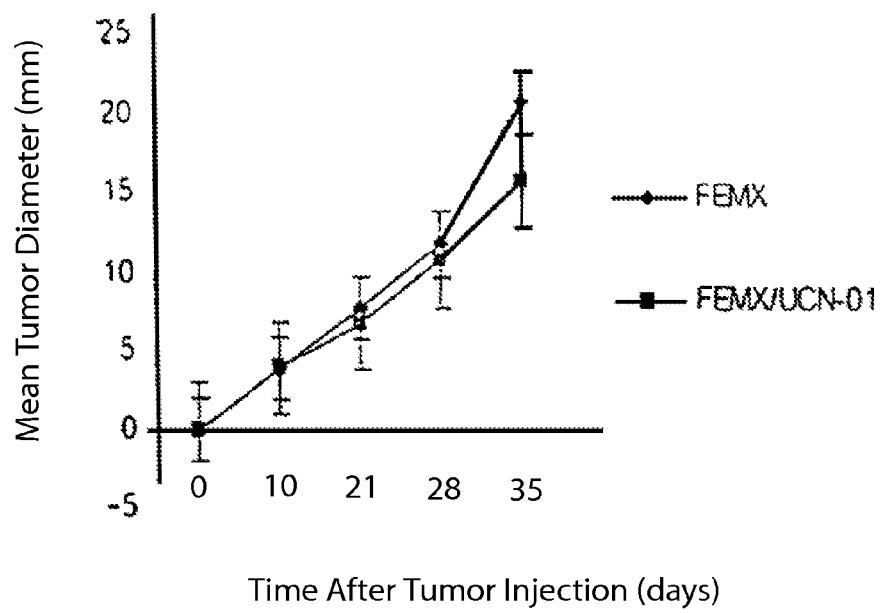
FIG. 7A shows the growth of transplanted FEMX tumor cells in untreated mice (-□-) and in mice treated with the chemotherapeutic UCN-01 (-□-).
Figure 7B:
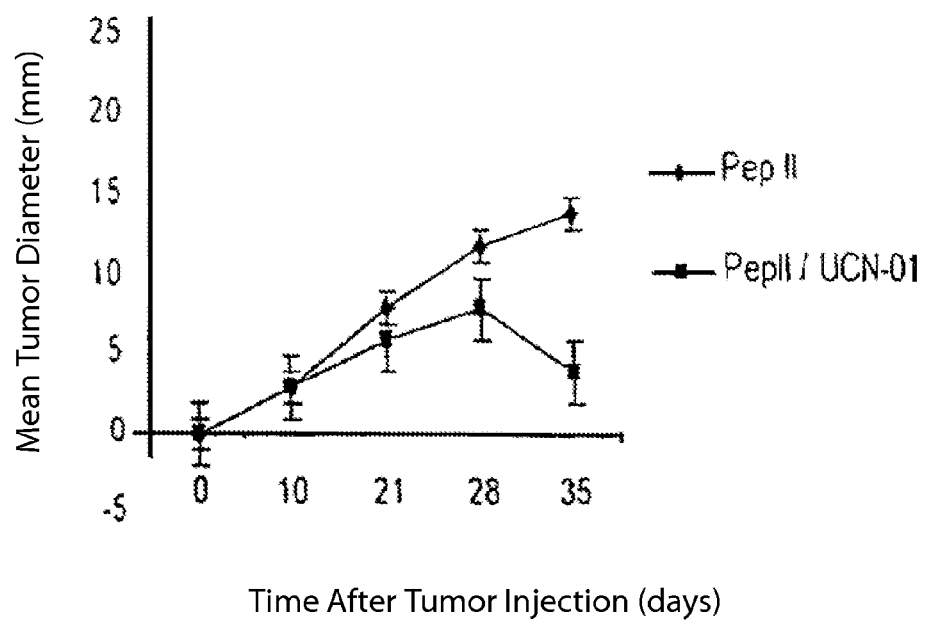
FIG. 7B shows the growth of transplanted FEMX tumor cells expressing peptide II in untreated mice ( —▯— )and in mice treated with the chemotherapeutic UCN-01 ( —▯— )
Figure 7C:
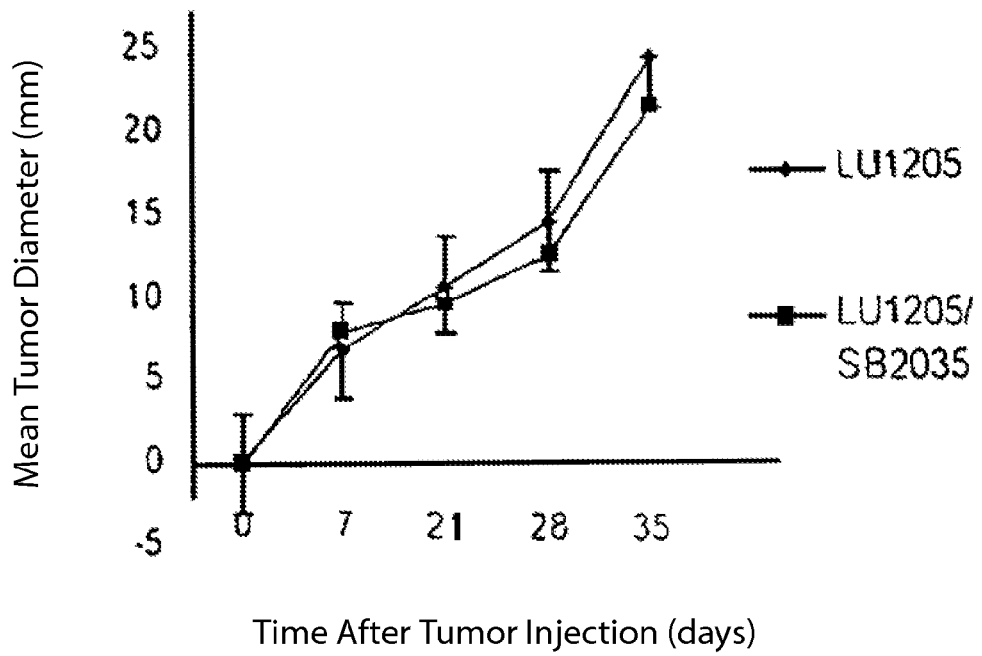
FIG. 7C shows the growth of transplanted LU1205 tumor cells in untreated mice ( —▯— )and in mice treated with the p38/JNK kinase inhibitor SB2035 ( —▯— ).
Figure 7D:
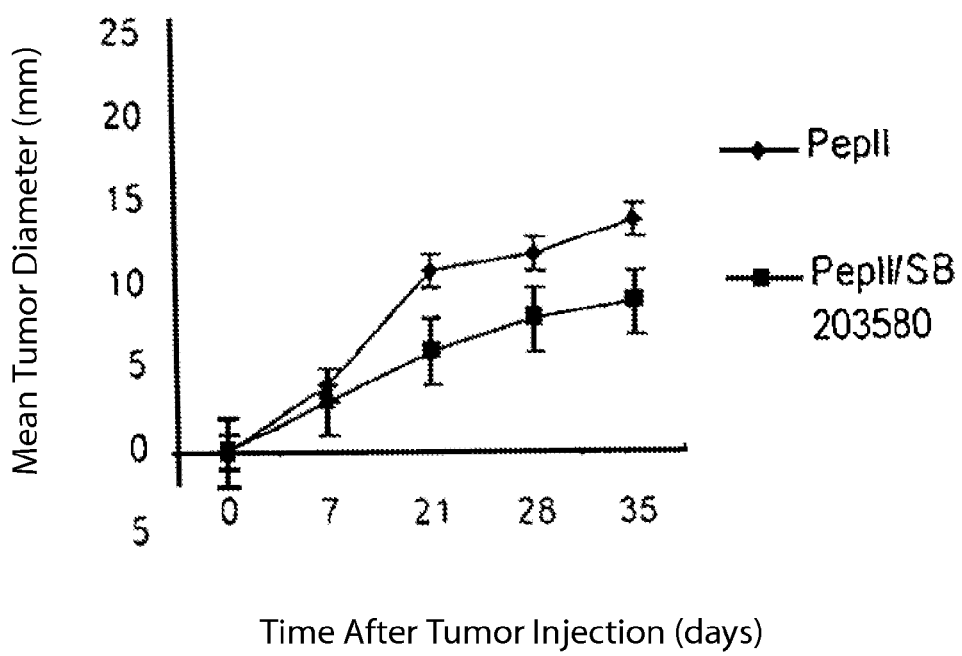
FIG. 7D shows the growth of transplanted LU1205 tumor cell expressing peptide II in untreated mice ( —▯— )and in mice treated with the chemotherapeutic SB2035 ( —▯— )

Inhibition of melanoma cell growth by peptide II and chemotherapy or a p38/JNK kinase inhibitor in vivo. The FEMX and LU1205 melanoma tumor cell lines were transplanted into mice. Untreated control animals showed significant tumor cell growth of both tumors; administration of the chemotherapeutic UCN-01 to FEMX cells had little effect, if any (FIG. 7A). Similarly, the p38/JNK kinase inhibitor SB2035 had almost no effect on LU1205 cells (FIG. 7C). However, cells that expressed peptide II grew much more slowly (FIGS. 7B and 7D). Co-treatment of FEMX cells with peptide II and UCN-01 caused tumor regression (FIG. 7B). The combination of peptide II and SB203580 was also more effective in inhibiting LU1205 cell growth (FIG. 7D).

Mouse SW1 tumors that express peptide II grow to a smaller size. SW1 cells that constitutively express peptide II or control vector were injected SC into C3H mice and tumors were analyzed three weeks later. Control cells that contained a null vector develop large and massive tumors, which would metastasize shortly after. Tumor cells that expressed peptide II developed very small tumors. SW1 melanoma tumors metastasize to the lungs and chest wall in control vector expressing cells, but not in cells that express peptide II.

Figure 8A:
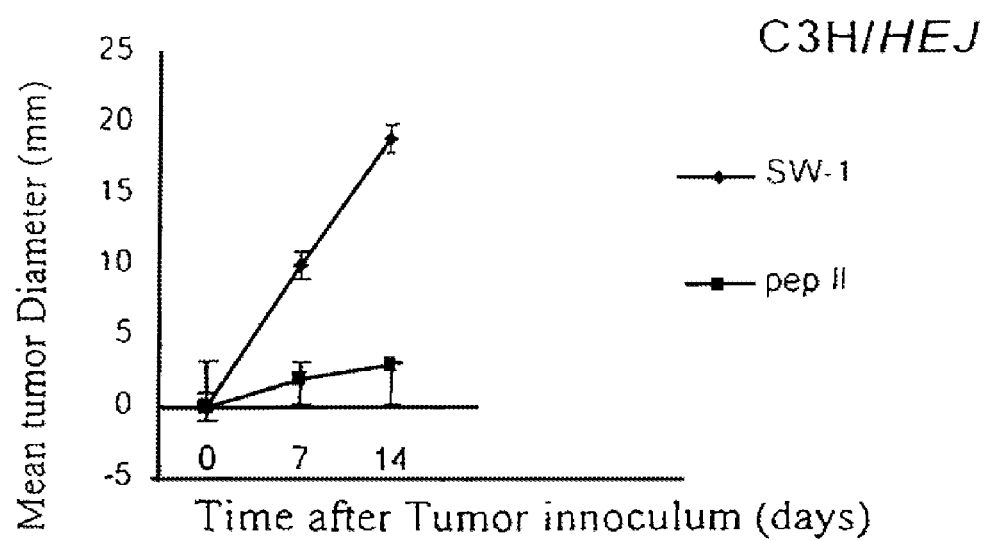
FIGS. 8A-8B show the growth of SW1 cells that express control ( —▯— )or peptide II ( —▯— )in mice over a 14 day period. The SW1 cells were subcutaneously injected in C3H (FIG. 11A) and GLD (FIG. 11B) mice.
Figure 8B:
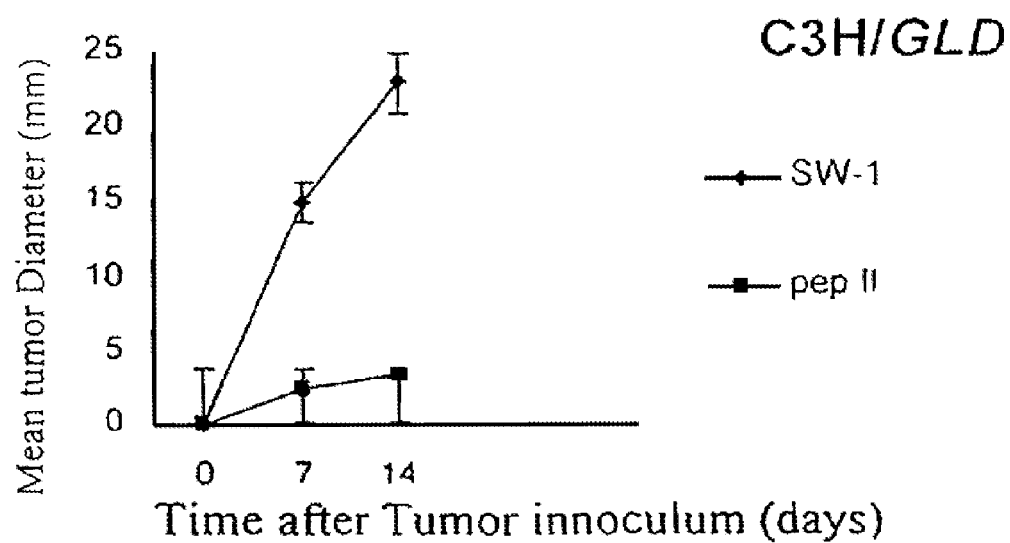

SW1 cells that express control or peptide II were injected SC into C3H or GLD (Fas ligand knockout) mice and the size of tumors monitored for two weeks. At the end of this time, tumors were excised and measured or subjected to histopathological analysis. Tumors were found to have significant growth inhibition with expression of the peptide II vector, particularly compared to control cells (FIG. 8). Because of the rapid growth of the control parent tumor, parallel monitoring of the growth of the parent versus peptide II-expressing SW1 tumors was limited to a 3-week period, at which point the differences in the growth rate of the peptide II-expressing SW1 cells was even more pronounced (100 mm$^3$ compared with 1800 mm$^3$). This striking difference suggests that expression of peptide II sufficed to inhibit growth of this aggressive melanoma. The expression of peptide II was as efficient in blocking growth of SW1 tumors in FasL-deficient GLD mice (FIG. 8B), suggesting that the Fas pathway may not serve as the primary mechanism for sensitization of the ATF2 peptide-expressing tumors to apoptosis.

Figure 8C:
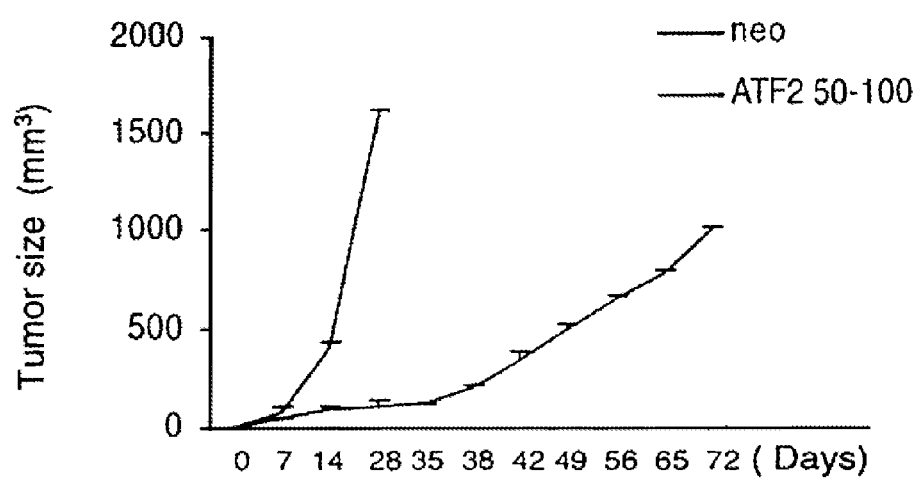
FIG. 8C shows the growth of SW1 cells that express either control (top curve) or peptide II (bottom curve) after growth was monitored for up to 72 days.

Whereas the growth of SW1 tumors was such that they had to be removed by about day 20, as tumors developed to the size of about 1700 mm$^3$, SW1 cells that express peptide II were monitored up to 72 days, at which point the tumors had reached an average size of about 1200 mm$^3$ (FIG. 8C). These data suggest that expression of peptide II significantly reduced the growth rate of the SW1 tumors. Indeed growth of the SW1 tumors was completely blocked up to 35 days, after which these tumors grew, albeit at a slower rate than that of the parent cells (FIG. 8C). The change in growth rate could result from changes to the tumor during progression, e.g., development of resistance to ATF2 activity. Expression of the ATF2 peptide in the actual tumors excised after 72 days was confirmed via immunohistochemistry, revealing that most of the tumor expressed the ATF2 peptide. This expression was not uniform across the tumor suggesting that changes seen in the growth rate after 35 days could be also attributed to select cell population that no longer express ATF2 peptide. Analysis of SW1 tumors via the tunnel assay revealed a substantially higher level of apoptosis in tumors that expressed the peptide II. These findings suggest that the mechanism underlying the inhibition of SW1 growth in vivo can in part be attributed to increased basal levels of apoptosis.

Expression of peptide II in SW1 mouse melanoma cells inhibits their metastatic capacity. SW1 cells are prone to metastasize into multiple organs, resulting in multiple lesions as early as 4 weeks following injection (Owen-Schaub L. B., et al., J. Exp. Med. 1998; 188:1717-1723). However, no metastasis was seen in any of the multiple experiments and settings where peptide II-expressing SW1 cells were monitored, up to 72 days. This finding suggests that expression of peptide II efficiently inhibits the formation of metastasis in this model. In all, these findings indicate that constitutive expression of peptide II is sufficient to inhibit metastasis and markedly reduce growth of the aggressive SW1 melanoma tumor.

Figure 9:
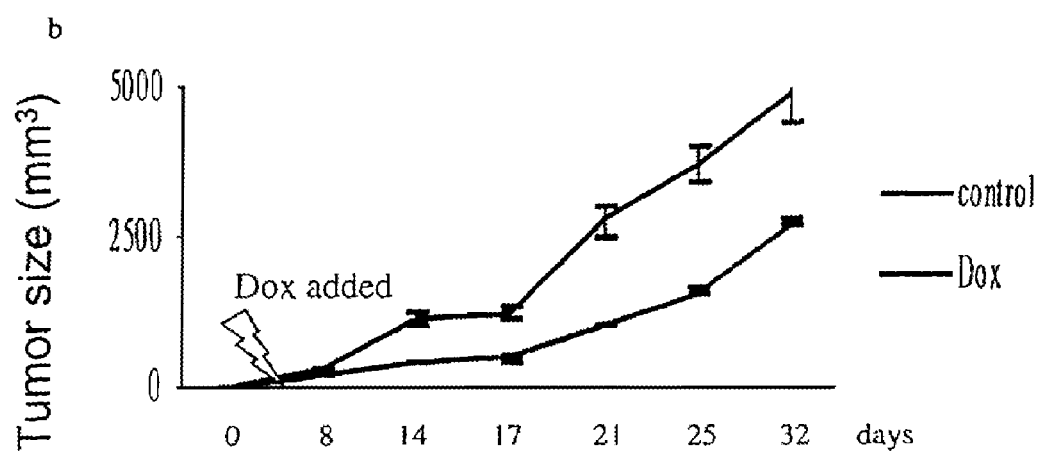
FIG. 9 shows the doxycycline-inducible controlled in vivo expression of peptide II in SW1 cells. Positive clones were selected for injection into C3H mice. Induction of expression was controlled by the addition of doxycycline to drinking water (500 µg/ml). This figure demonstrates tumor growth of dox-induced peptide II expressing SW1 cells (lower curve) as compared with untransfected control SW1 cells (top curve) (P<0.003). The data shown represent 6 animals per group.

Inducible expression of peptide II suffices to attenuate growth and metastasis of existing SW1 tumors. The striking inhibition of growth of SW1 tumors that constitutively express peptide II led us to explore whether expression of this peptide in existing tumors affects their growth. We cloned the cDNA of peptide II into a dox-inducible expression vector. Cultures of single SW1 clones that express peptide II after addition of doxycycline were selected. In this design, we allowed growth of tumors to the size of 90 mm$^3$ before adding doxycycline to the drinking water to induce peptide expression. Tumor growth was monitored for 32 days, the last 24 of which were in the presence of doxycycline. Under these conditions inducible expression of peptide II caused about a 2-fold decrease in the growth rate of SW1 tumors (FIG. 9). Tumors excised from doxycycline-fed mice exhibited an increase in degree of apoptosis as revealed from tunnel assay. Immunohistochemistry revealed partial expression of peptide II in tumors developed in doxycycline-fed mice, explaining the limited nature of the differences seen when compared with the constitutive expression of the peptide.

Figure 10A:
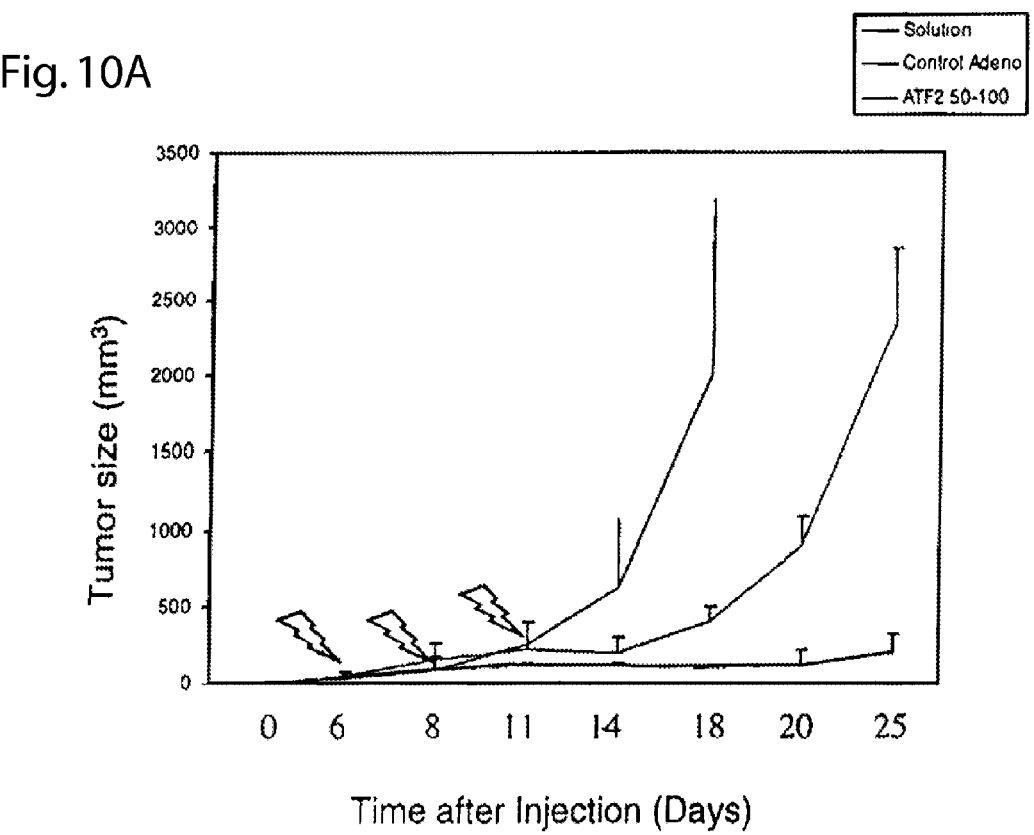
FIGS. 10A and 10B demonstrate tumor growth curves of B16F10 melanomas in C57BL6 mice.

In a parallel approach, the cDNA of peptide II was cloned into an adenovirus vector and administered to SW1 tumors (40 mm$^3$ in size) via direct intra-tumoral injection. Whereas no difference in tumor growth rate was seen within the first week after injection, a marked reduction (about 50%) in tumor growth was observed shortly after the second injection (FIG. 10A). A corresponding decrease was also found in the weight of SW1 tumors injected with adenovirus-expressing peptide II, as compared with the corresponding controls. These data suggest that limited expression of peptide II into already developed melanoma elicits efficient reduction of subsequent tumor growth. These findings confirm the physiological relevance for the observation that expression of peptide II efficiently reduces further growth of this aggressive melanoma.

Figure 10B:
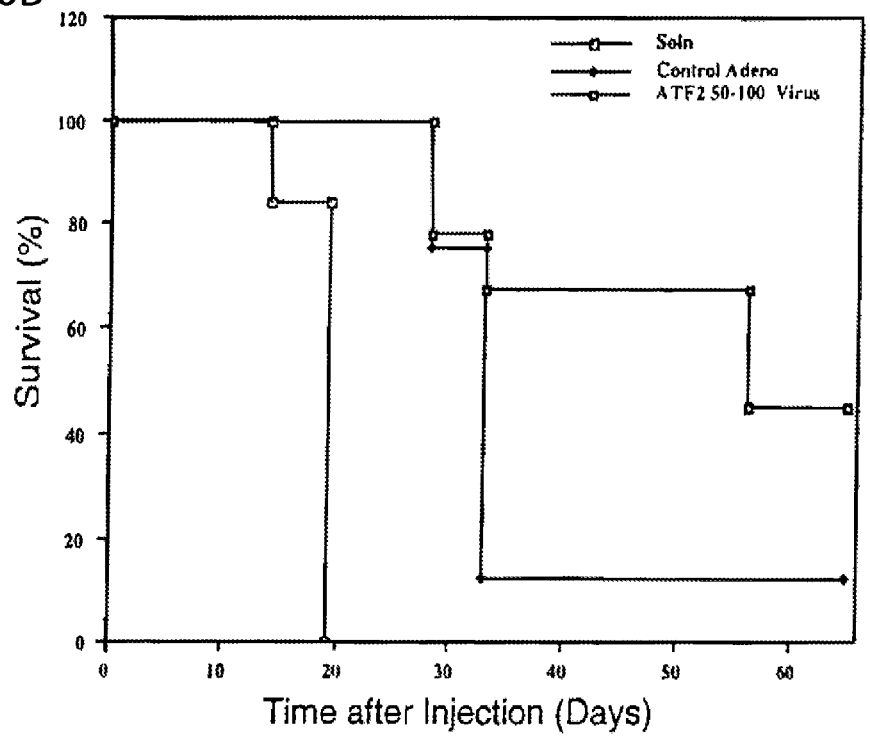

Regression of B16F10 melanoma following injection of peptide II. To further assess the effect of peptide II on growth and metastasis of melanoma, we tested the aggressive B16F10 melanoma in C57BL mice. Injection of adenovirus bearing peptide II into eighteen B16F10 tumors (one per mice) that had reached the size of 40 mm$^3$ had no effect on four tumors (22%) but caused complete regression in seven (39%) and reduced the growth of seven tumors. Importantly, fourteen out of eighteen animals injected with peptide II had no metastatic lesions when compared with the parent tumors. The differences seen among the three experimental groups (control, virus control and the peptide II adenovirus) are significant (P<0.0001) based on Tukey's Multiple Comparisons (HSD). Survival and fraction of tumor free animals was higher in the group treated with peptide II (FIG. 10B). These findings suggest that in vivo administration of the peptide via an adenovirus vector suffices for efficient inhibition of growth up to a complete regression of B16F10 tumors.

Discussion

The results presented here demonstrates the ability of a relatively short peptide derived from the ATF2 transactivating domain to alter melanoma growth and metastasis capacity in vivo using three different model systems and three different modes of expression: (i) constitutive expression of the ATF2 peptide in SW1 mouse melanoma cells is sufficient to result in strong inhibition of tumor growth and abolishment of metastasis; (ii) inducible expression of the ATF2 peptide via doxycycline in SW1 tumors efficiently reduces their growth rate by 50% despite achieving only partial expression in the overall tumor mass; (iii) administration of ATF2 peptide by intra-tumoral injection of an adenovirus that expresses the peptide is sufficient to cause a significant inhibition of SW1 growth; (iv) using a different mouse model, B16F10, intra-tumoral injection of adenovirus carrying ATF2 peptide caused inhibition of growth or complete regression in greater than 80% of the animals, with corresponding inhibition in metastasis. Expression of the peptide in human melanoma tumors transplanted into nude mice efficiently slowed tumor progression in combination with a chemotherapeutic drug or inhibitor of stress kinases. Inhibition and regression of melanomas in response to inducible expression of the peptide II or its administration via an adenovirus reflect relevant physiological scenarios. Taking all these findings together, peptide II emerges as an efficient reagent that is capable of altering melanoma growth and metastatic potential.

The anti-melanoma efficiency of peptide II appears to be dependent on the characteristics of the tumor to which it is targeted. Unlike the almost complete inhibition of mouse SW1 tumor growth seen for the first 35 days, and complete regression in some of the B16F10 tumors resulted from expression of peptide II, the effect on the two human tumors tested was limited and required further treatment with chemotherapeutic or pharmacological inhibitors to achieve satisfactory efficacy. The difference among tumors could be attributed to differences in genetic and epigenetic background, which are likely to vary in these tumors. In support of the differences among the human and mouse tumors is the finding that each is sensitized to a different spectrum of kinase inhibitors.

Changes in the effectiveness of peptide II could be also attributed to alteration of the immune response, either by the tumorigenicity of the different tumors or by changes elicited by the peptide that may trigger better immune recognition. The use of immunologically impaired nude mice for the analysis of the human tumors may also explain the nature of differences seen in the effectiveness of peptide II between the human and mouse tumor models. It is important to note that the activities of the ATF2 peptide described here require that certain changes, yet to be determined, take place during melanoma development and progression, inasmuch as the peptide II does not elicit sensitization of early-stage melanoma-derived cells or melanocytes (Bhoumik et al., Clin. Cancer Res. 2001; 7(2):331-42). That ATF2 knockout mice do not exhibit susceptibility to tumor development but rather, exhibit phenotypes limited to neurological disorders (Reimold A. M., et al., Nature 1996; 379:262-265) further suggests that ATF2's ability to effect melanoma phenotypes associated with resistance and metastasis requires additional genetic and epigenetic changes.

The sensitization of human melanomas to treatment by either the pharmacological inhibitor of p38 or by the chemotherapeutic drug UCN-01 points to an important advance in treatment of these tumors by reagents that otherwise do not affect this tumor type. We must emphasize that our studies in the SW1 and B16F10 tumor settings were limited to the effect of peptide II alone as it was sufficient to elicit striking inhibition of these aggressive tumors. It is expected that the effects of peptide II on tumor growth rate and metastasis would be improved by combining the peptide II with other treatments, including inhibitors of stress kinases, immunological modulators, or chemotherapeutic drugs.

The efficient effect of peptide II was seen in cells that constitutively express peptide II, where there was a complete inhibition of growth up to 35 days, and a complete inhibition of metastasis with marked reduction of growth up to 72 days following injection. Changes in the biology of the tumors studied over time may limit peptide II's effect requiring assistance by means of other therapeutic factors: this is among the possibilities that would explain the reduced effectiveness seen 35 days after inoculation of the SW1 cells that express this peptide. However, we cannot exclude the possibility that a sub-population of SW1 cells either lost or developed means to override the effects of peptide II. As one example, the doxycycline-based regulated expression of peptide II resulted in less efficient tumor cell apoptosis because expression was limited to a subset of tumor cells. This is explained by the different modes of selection (puromycin that was provided as a co-expressing vector for the dox-inducible constructs versus neomycin, which was part of the construct that constitutively expressed peptide II).

Incomplete expression of peptide II is expected to result in peptide-free cells that exhibit phenotypes similar to those seen in the parent cells that lack peptide II. Indeed, immunohistochemistry analysis of the tumors excised from dox-treated mice revealed partial expression of peptide II, which could account for the lower degree of growth inhibition and the appearance of metastasis. Of interest, administration of peptide II via adenovirus-mediated intra-tumor injection reduced the growth of SW1 tumors by 50%, further supporting the importance of efficient delivery to achieve maximal tumor inhibition. In contrast, the marked effects of ATF2 peptide on B16F10 tumors further support that efficient expression is one important parameter whereas the biology of the tumor serves an equally important role in dictating the effectiveness of the ATF2 peptide.

Example 3

Peptide II Alters Transcriptional Activities of ATF2/c-Jun and Alters FAS Receptor Expression To determine mechanisms underlying peptide II's ability to inhibit tumorigenicity and metastasis of the aggressive melanoma models studied here, we assessed possible changes in transcriptional activities of ATF2 and its heterodimeric partner c-Jun.

Materials and Methods

Transient transfection and transcriptional analysis. Mouse melanoma tumors grown in culture were transfected with control vector or peptide II expressing luciferase or β-galactosidase constructs (Bhoumik et al., Clin. Cancer Res. 2001; 7(2):331-42). Transient transfection of different reporter constructs (0.5 cg) with expression vectors and pCMV-$_c$gal (0.25 Cg) into $5 \times 10^5$ melanoma cells was performed using Lipofectamine™ (Life Technologies-BRL). Transfection of the Jun2-luciferase construct permitted us to monitor activity of ATF2 and c-Jun. Jun2-Luc and TRE-Luc constructs were previously described (van Dam H., et al., EMBO J. 1993; 12:479-487; and van Dam H., et al., EMBO J. 1995; 14:1798-1811). Luciferase activity was determined using the Luciferase assay system (Promega®, Madison, Wis.) and normalized on the basis of β-galactosidase (β-Gal) levels in transfected cells. Proteins were prepared for β-Gal and Luciferase analysis at the selected time points after transfection.

Analytical Tests.

Electrophoretic mobility shift assays were performed as described. (Ivanov and Ronada, J Biol Chem 1999; 274(20): 14079-89). GST binding assays were performed with GST-peptide II as described (Adler et al., Proc Natl Acad Sci USA 1995; 92 10585-9). SW1 cells expressing control vector or peptide II were subjected to FACS analysis following their incubation with antibodies to the cell surface receptor of FAS as described above.

Results

Peptide II inhibits ATF2 transcriptional activity of ATF2/c-Jun. Previous studies revealed a 3-fold inhibition of transcriptional activity mediated from the AP1 complex, suggesting that the expression of peptide II downregulates the transcriptional activity of ATF2.

To confirm these studies, SW1 cells were transfected with peptide II and mixed cell populations that exhibit constitutive expression of this peptide or a control empty construct were selected. Using the consensus ATF2 target sequence that consists of the motif found on c-Jun promoter (TGACACTA), we carried out electrophoretic mobility shift assays. No significant changes were observed in binding of nuclear extracts prepared from control and peptide II-expressing SW1 cells to the labeled AP1 oligonucleotide. In contrast to the DNA binding assay, transfection of Jun2-Luciferase reporter gene into SW1 clones that constitutively express peptide II revealed a 5-fold decrease in basal levels of ATF2 transcriptional activities. A decrease in ATF2 transcriptional activities was also seen in response to UV-treatment. These findings suggest that peptide II interferes with endogenous ATF2 and/or c-Jun transcriptional activities. Since it is not possible to distinguish between Jun and ATF2 transcriptional activities when using this target sequence, we performed similar analyses in c-Jun and ATF2 null cells.

A marked inhibition of transcriptional activity meditated from the Jun2 promoter was also seen in Jun null fibroblasts, similar to that observed in the SW1 cells. These findings strongly suggest that ATF2 transcriptional activities are inhibited upon the expression of peptide II. Expression of peptide II in ATF2 null cells did not affect Jun2-Luc activities, further supporting the notion that this peptide primarily inhibits ATF2 transcriptional activities and demonstrating the specificity of this peptide. While the Jun2 sequence is primarily regulated by ATF2/Jun heterodimers, the TRE motif is regulated primarily by c-Jun/c-fos as well as by other members of the AP1 transcriptional complex. To determine whether the expression of peptide II affects transcription from TRE-based promoters, we analyzed TRE-Luc activity in c-Jun wild-type fibroblasts. Surprisingly, expression of peptide II caused a 200-fold increase in the activities of TRE-Luc. These findings suggest that while suppressing ATF2 activities, expression of the ATF2 peptide suffices to increase transcriptional activities of the c-Jun or Jun family members that recognize the AP1 target sequence.

To further elucidate the nature of the peptide II's ability to impair ATF2 mediated transcription, we determined whether peptide II binds to these transcription factors or to their corresponding kinases. GST-peptide II was used for these binding assays, which revealed a specific association with ATF2, but not with c-Jun. Further, JNK in its active form, was also bound to GST-peptide II, as revealed by binding assays, which demonstrated greater binding in extracts of UV-treated cells. JNK association with ATF2 peptide was formally shown to require amino acid residues 40-60 of ATF2 (Fuchs, S. Y., et al., J. Biol. Chem. 1997; 272:32163-32168). Neither JNK nor p38 was found capable of phosphorylating peptide II in vitro. This observation suggests that the peptide may lack the complete conformation required for recognition as substrate by kinases. A larger region of the amino-terminal ATF2 domain (amino acid residues 1-115) used in parallel experiments exhibits equivalent association with f1 JNK but weaker association with ATF2 or the phosphorylated form of ATF2, suggesting that the size or conformation of the smaller peptide enables its better association with ATF2, although the site of association is yet to be identified. Thus, peptide II may elicit its inhibitory functions on ATF2 by out-competing the phosphorylation of endogenous ATF2, thereby decreasing the availability of its transcriptionally active form. Alternatively, through its association with the endogenous ATF2, peptide II may interfere with assembly of the transcription initiation complex, which would result in decreased transcriptional activities. The marked increase in the transcriptional activities of c-Jun or its family members can be indirect, due to the effect on ATF2, or direct, via effect of peptide II on members of Jun family (e.g., inhibition of Jun B).

Given the ubiquitous nature of c-Jun in the transcriptional regulation of cellular genes, altered balance of ATF2 and Jun family members due to the expression of peptide II is expected to modify the expression of genes regulated by these transcription factors with a concomitant changes on cellular regulatory functions. Indeed, analysis of possible changes in growth rate of cells that express peptide II revealed a 50% reduction in DNA synthesis level based on thymidine incorporation assays (FIG. 11A). Similarly, monitoring the rate of cell growth revealed a corresponding decrease in the number of SW1 cells that express peptide II. Further insight to the effect of peptide II on growth of SW1 cells comes from analysis of cell cycle distribution. The number of peptide II-expressing cells found to be in the S-phase 18-24 h after serum stimulation of synchronized cells was 2-fold lower than in the control cell population (FIG. 11B). This finding suggests that peptide II-expressing cells exhibit a delayed entrance into, and exit from, the S-phase. Collectively, these data suggest that peptide II altered expression of genes that play a role in growth control, DNA synthesis and possible regulation of the cell cycle.

Peptide II alters FAS receptor expression in SW1 tumor cells. SW1 cells expressing control vector or peptide II were subjected to FACS analysis following their incubation with antibodies to the cell surface receptor of FAS. Changes in FAS levels were observed upon expression of peptide II relative to control cells; peptide II greatly increased the level of FAS on the cells.

Discussion

Inhibition of ATF2 transcriptional activities, while increasing those of c-Jun family members, is likely to represent the primary mechanism underlying the effects seen upon expression of peptide II. This conclusion is supported by the findings that cells expressing this peptide exhibit reduced transcriptional activity monitored from the Jun2 promoter but exhibit a remarkable increase in activity mediated by the TRE-Luc. The latter also coincided with the lack of peptide II's effect in ATF2 null cells, further demonstrating that inhibition is selective for promoters that are responsive to ATF2. The mechanisms underlying this inhibition could be attributed to the ability of peptide II to associate with ATF2 as well as JNK, through which it interferes with the phosphorylation of ATF2, cellular translocation or assembly of the transcription initiation complex. The marked increase in transcriptional activities of c-Jun and its family members could be either a consequence of ATF2 inhibition, or be due to the effect of ATF2 on c-Jun or its family members, e.g., inhibition of JunB or potentiation of JunD activities.

Due to reduced ATF2 and elevated transcriptional activities of Jun family members, gene profiling analysis revealed a large subset of genes that are regulated by ATF2 and c-Jun were found to exhibit altered expression—as shown infra in FIG. 12—for elevated TNF-related genes and down-regulation of growth-associated and IFN-related genes (see Example 4). The down-regulation of growth-associated and IFN-related genes is reflected in a marked reduction in the rate of DNA synthesis, changes in cell cycle distribution and sensitization of cells that express peptide II to undergo apoptosis following treatments which otherwise do not affect this tumor type.

Example 4

Microarray Gene Expression Profiling of SW1 Tumors Expressing Peptide II

To elucidate the molecular pathways affected by the expression of peptide II, we compared the RNA expression profiles of SW1 tumors that either express peptide II or a control vector by cDNA microarray analysis. This analysis is warranted in light of the ability of ATF2 peptide to increase transcriptional activities of Jun and its family members, while inhibiting those of ATF2. Given that c-Jun and its family members play key role in the regulation of a large set of genes, a corresponding change in gene expression profile is expected in cells that express ATF2 peptide. Genes that were either up- or down-regulated by greater then 2.5-fold were identified on the basis of a scatter plot analysis.

Methods cDNA microarray hybridizations. The 10 k mouse Gem 2 gene set (Incyte Genomics Inc, Palo Alto Calif.) was printed at the NCI on poly-L lysine coated glass using Biorobotics TASII arrayer (Cambridge, England). All protocols for the manufacturing and hybridization of microarrays are available at the NCI web site. Approximately 20 μg of total RNA was used in the reverse transcription reaction to directly label the probe with either Cy-5 dUTP or Cy-3 dUTP (Amersham®). Hybridizations were performed at 65° C. for 12-18 h in a hybridization volume of 35 ml. The hybridized arrays were scanned using an Axon GenePix 4000® scanner (Union city, CA) and fluorescent data were collected using GenePix™ software.

Data Analysis. The axon image data for each microarray was uploaded to the NCI mAdb database for subsequent analysis using a variety of statistical web based tools. Gene clustering analysis was performed using the clustering algorithm and tree view software developed by Mike Eisen (Stanford, Calif.).

Results and Discussion

Clustering analysis of the array data revealed that a large group of tumor necrosis factor-related genes were strongly upregulated in tumors that express peptide II Table 1, below. In addition, tumor suppressor genes and tumor rejection antigens were also clustered within this group. Of interest, and in accordance with our results in the current study, we observed downregulation of Fas-associated genes in tumors that express peptide II (Table 1, below). Down-regulation of Fas-associated genes would suggest that the Fas pathway is not the primary death pathway and explain why there was no change in the growth and development of these tumors in GLD mice, which are deficient in Fas ligand. Concomitant with decreased expression of Fas-associated genes was the upregulation of TNF-related transcripts, which constitute another major apoptosis cascade. These changes reveal that expression of peptide II efficiently altered the balance of apoptosis cascades from Fas toward the TNF pathway, which otherwise provides a pro-mitogenic signal in these late-stage melanomas (Ivanov, V. N., et al., J. Biol. Chem. 1999; 274: 14079-14089; and Ivanov V. N., et al., Oncogene 2001; 20:2243-2253). Interestingly we also observed a consistent downregulation of growth-associated genes including epidermal growth factor, hepatoma-derived growth factor and insulin like growth factor, and several interferon-associated genes.

TABLE 1

| EISEN CLUSTER ANALYSIS | |
| --- | --- |
| Upregulation of Tumor Necrosis Factor Superfamily and Other Tumor Antigens | tumor necrosis factor induced protein 6<br>large tumor suppressor 2<br>tumor necrosis factor receptor superfamily, member<br>tumor protein D52<br>*Mus musculus* N14A tumor-related protein<br>tumor necrosis factor, alpha-induced protein<br>suppression of tumorigenicity<br>type 1 tumor necrosis factor receptor shedding aminopeptide |

TABLE 1-continued

EISEN CLUSTER ANALYSIS

| | |
|---|---|
| | tumor protein D52 |
| | mammary tumor integration site 6 |
| | tumor necrosis factor receptor superfamily |
| | natural killer tumor recognition sequence |
| | tumor rejection antigen gp96 |
| Downregulation of Fas-Associated Genes | Fas-associating protein with death domain |
| | Fas death domain-associated protein |
| | Fas-activated serine/threonine kinase |
| Downregulation of Growth Associated Genes | epidermal growth factor receptor |
| | epidermal grown factor receptor pathway substrate |
| | insulin-like growth factor binding protein 4 |
| | growth arrest DNA-damage-inducer |
| | nerve growth factor receptor (TNFI) |
| | inhibitor of growth family, member 1 |
| | hepatoma-derived growth factor, related protein 2 |
| | hepatocyte growth factor-like |
| | hepatoma-derived grown factor, related protein 3 |
| | insulin-like grown factor binding |
| | insulin-like growth factor binding protein 4 |
| Downregulation of Interferon Associated Genes | interferon-g induced GTPase |
| | interferon regulatory factor 7 |
| | ATP-dependant interferon responsive |
| | interferon-induced protein with tetratricopeptide |
| | interferon-stimulated protein (15 kDa) |
| | interferon activated gene 204 |

Among additional genes found to be both up- and downregulated in four independent experiments were ATF2, which was downregulated in tumors expressing peptide II, further supporting the basic premise that the peptide used here downregulates ATF2 at the expression and transcriptional levels. Coincident with decreased ATF2 was increase in the expression of ATF4 transcripts, the significance of which is yet to be determined. Among other up-regulated transcripts were interleukin-1 beta (implicated in inhibition of angiogenesis and metastasis of melanoma and other tumors (Belardelli, F., et al., Int. J. Cancer 1989; 44(6): 1108-16), cullin 3 (ubiquitin protein ligase, which controls cyclin E ubiquitination and consequently regulates entry into the S-phase (Singer, J. D., et al., Genes Dev. 1999; 13(18):2375-87; Winston, J. T., et al., Genes Dev. 1999; 13:2751-7), kinesin-associated protein 3 (a kinesin superfamily-associated protein implicated in organelle transport (Yamazaki, H., et al., Proc. Natl. Acad. Sci. USA 1996; 93; Manning, B. D., et al., Cell Biol. 2000; 10(7):281-9), ATF3 (which represses the cyclic-AMP responsive element, (CRE)-dependent transcription, and accelerates caspase protease activation during DNA damaging agent-induced apoptosis (Mashima, T., et al., J. Cell Physiol. 2001; 188(3):352-8) and membrane metallo-endopeptidase (implicated in invasion and metastasis (Hofmann, U. B., et al., J. Invest Dermatol. 2000; 115(3):337-44).

Among the additional transcripts that were downregulated in ATF2-expressing tumors were tyrosine kinase 2, metallothionein 2 (which confers resistance to metals (Czaja, M. J., et al., J. Cell Physiol. 1991; 147(3):434-8), ubiquitin-specific protease 18 (a type I interferon-inducible gene that contributes to growth arrest and differentiation in human melanoma cells treated with IFN-b (Kang, D., et al., Gene 2001; 267(2): 233-42). Overall, this analysis provides important mechanistic insights into changes in the expression pattern of genes that occurred in vivo in the course of inhibiting tumor growth as a result of the expression of peptide II.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

REFERENCES

1. Meier, F., Satyamoorthy, K., Neit, M., Hsu, M.-Y., Schittek, B., Garbe, C., and Herlyn, M. Molecular events in melanoma developments and progression. Frontiers in Bioscience, 3: d1005-1010, 1998.
2. Ashkenazi, A., and Dixit, V. M. Death receptors: Signaling and modulation. Science, 281: 1305-1308, 1998.
3. Nagata, S. Apoptosis by death factor. Cell, 88: 355-365, 1997.
4. Peli, J., Schroter, M., Rudaz, C., Hahne, M., Meyer, C., Reichmann, E., and Tschopp, J. Oncogenic ras inhibits Fas ligand-mediated apoptosis by downregulating the expression of Fas. EMBO J., 18: 1824-1831, 1999.
5. Deveraux, Q., and Reed, J. C. IAP family proteins—suppressors of apoptosis. Genes & Dev., 13: 239-252, 1999.
6. Moretti, S., Pinzi, C., Spallazani, A., Berti, E., Chiarugi, A., Mazzoli, S., Fabiani, M., Vallecchi, C., and Herlyn, M. Immunohistochemical evidence of cytokine networks during progression of Fas. Int. J. Cancer, 20: 160-168, 1999.
7. Hsu, H., Shu, H.-B., Pan, M.-G., and Goeddel, D. V. TRADD-TRAF2 and TRADD-FADD interactions define two distinct TNF receptor 1 signal transduction pathways. Cell, 84: 299-308, 1996.
8. Liu, Z.-G., Hsu, H., Goeddel, D. V., and Karin, M. Dissection of TNF receptor 1 effector functions: JNK activation is not linked to apoptosis while NF-kB activation prevents cell death. Cell, 87: 565-576, 1996.
9. Arch, R. H., Gedrich, R. W., and Thompson, C. B. Tumor necrosis factor receptor-associated factors (TRAFs)—a family of adapter proteins that regulates life and death. Genes & Dev., 12: 2821-2830, 1998.
10. Johnson, J. Cell adhesion molecules in the development and progression of malignant melanoma. Cancer Metastasis Rev., 18: 345-357, 1999.
11. Wang, R. Human tumor antigens: implications for cancer vaccine development. J. Mol. Med., 77: 640-655, 1999.
12. Ramaswamy S, Nakamura N, Vazquez F, Batt D B, Perera S, Roberts T M, Sellers W R. Regulation of G1 progression by the PTEN tumor suppressor protein is linked to inhibition of the phosphatidylinositol 3-kinase/Akt pathway. Proc Natl Acad Sci USA. 96: 2110-5, 1999
13. Zhou X P, Gimm O, Hampel H, Niemann T, Walker M J, Eng C. Epigenetic PTEN silencing in malignant melanomas without PTEN mutation. Am J. Pathol. 157: 1123-8 2000.

14. Krasilnikov, M., Adler, V., Fuchs, S. Y., Dong, Z., Haimoviz-Friedman, A., Herlyn, M., and Ronai, Z. Contribution of phosphatidylinositol 3-kinase to radiation resistance in human melanoma cells. Mol. Carcinogenesis, 24: 64-69, 1999.

15. Jiveskog, S., Ragnarsson-Olding, B., Platz, A., and Ringborg, U. N-ras mutations are common in melanomas from sun-exposed skin of humans but rare in mucosal membranes or unexposed skin. J. Invest. Dermatol., 5: 757-761, 1998.

16. Itoh, S., Hattori, T., Hayashi, H., Mizutani, Y., Todo, M., Takii, T., Yang, D., Lee, J., Matsufuji, S., Murakami, Y., Chiba, T., and Onozaki, K. Antiproliferative effect of IL-1 is mediated by p38 mitogen-activated protein kinase in human melanoma cell A375. J. Immunol., 162: 7434-7440, 1999.

17. Ivanov, V. N., and Ronai, Z. p38 protects human melanoma cells from UV-induced apoptosis through down-regulation of NF-kB activity and Fas expression. Oncogene, 19: 3003-3012, 2000.

18. Ivanov, V. N., Kehrl, J. H., and Ronai, Z. Role of TRAF2/GCK in melanoma sensitivity to UV-induced apoptosis. Oncogene, 19: 933-942, 2000.

19. Barker, N., Morin, P., and Clevers, H. The Yin-Yang of TCF/beta-catenin signaling. Adv Cancer Res., 77: 1-24, 2000.

20. Soldatenkov V A, Dritschilo A, Ronai Z, Fuchs S Y. Inhibition of homologue of Slimb (HOS) function sensitizes human melanoma cells for apoptosis. Cancer Res. 59: 5085-8. 1999.

21. Rubinfeld B, Robbins P, El-Gamil M, Albert I, Porfiri E, Polakis P. Stabilization of beta-catenin by genetic defects in melanoma cell lines. Science. 275:1790-2, 1997.

22. Piepkorn, M. Melanoma genetics: An update with focus on the CDKN2A(p16)/ARF tumor suppressors. J. Am. Acad. Dermatol., 42: 705-726, 2000.

23. Yang, Y.-M., Dolan, L., and Ronai, Z. Expression of dominant negative CREB reduces resistance to radiation of human melanoma cells. Oncogene, 12:2223-2233, 1996.

24. Ronai, Z., Yang, Y.-M., Fuchs, S. Y., Adler, V., Sardana, M., and Herlyn, M. ATF2 confers radiation resistance to human melanoma cells. Oncogene, 16: 523-531, 1998.

25. Ivanov, V. N., and Ronai, Z. Down-regulation of tumor necrosis factor a expression by activating transcription factors 2 increases UVC-induced apoptosis of late-stage melanoma cells. J. Biol. Chem., 274:14079-14089, 1999.

26. Nicoletti, I., Migliorati, G., Pagliacci, M. C., Grignani, F., and Riccardi, C. A rapid and simple method for measuring thymocyte apoptosis by propidium iodide staining and flow cytometry. J. Immunol. Methods, 139: 271-279, 1991.

27. Gupta, S., Campbell, D., Derijard, B., and Davis, R. J. Transcriptional factor ATF2 regulation by the JNK signal transduction pathway. Science 267: 389-393, 1995.

28. Fuchs, S. Y. and Ronai, Z. Ubiquitination and degradation of ATF2 are dimerization dependent. Mol. Cell. Biol., 19: 3289-3298, 1999.

29. Graves P R, Yu L, Schwarz J K, Gales J, Sausville E A, O'Connor P M, Piwnica-Worms H The Chk1 protein kinase and the Cdc25C regulatory pathways are targets of the anticancer agent UCN-01. J Biol Chem 275:5600-, 2000.

30. Mack P C, Gandara D R, Bowen C, Edelman M J, Paglieroni T, Schnier J B, Gelmann E P, Gumerlock P H. RB status as a determinant of response to UCN-01 in non-small cell lung carcinoma. Clin Cancer Res. 259: 6-604, 1999.

31. Yu L, Orlandi L, Wang P, Orr M S, Senderowicz A M, Sausville E A, Silvestrini R, Watanabe N, Piwnica-Worms H, O'Connor P M. UCN-01 abrogates G2 arrest through a Cdc2-dependent pathway that is associated with inactivation of the Wee1Hu kinase and activation of the Cdc25C phosphatase. J Biol. Chem. 273:33455-64, 1998.

32. Gescher A Staurosporine analogues—pharmacological toys or useful antitumour agents? Crit. Rev Oncol Hematol. 34:127-35 2000.

33. Cuenda, A., Rouse, J., Doza, Y. N., Meier, R., Cohen, P., Gallagher, T. F., Young, P. R., Lee, J. C. SB 203580 is a specific inhibitor of a MAP kinase homologue which is stimulated by cellular stresses and interleukin-1. FEBS Lett., 364: 229-233, 1995.

34. Georgopoulos, K., Morgan, B. A., and Moore, D. D. Functionally distinct isoforms of the CRE-BP DNA-binding protein mediate activity of a T-cell-specific enhancer. Mol. Cell. Biol., 12: 747-757, 1992

35. Allan, A. L. Albanese, C., Pestsell, R. G., and LaMarre, J. (2001). Activating transcription factor 3 induces DNA synthesis and expression of cyclin D1 in hepatocytes. J. Biol. Chem. 276(29):27272-80.

36. Auer K. L., Contessa J., Brenz-Verca S., Pirola L., Rusconi S., Cooper G., Abo A., Wymann M. P., Davis R. J., Birrer M. and Dent P. (1998). The Ras/Rac1/Cdc42/SEK/JNK/c-Jun cascade is a key pathway by which agonists stimulate DNA synthesis in primary cultures of rat hepatocytes. Mol. Biol. Cell, 3:561-573.

37. Bar-Eli M. (1999). Role of AP-2 in tumor growth and metastasis of human melanoma. Cancer Metastasis Rev. 18:377-385.

38. Belardelli, F., Ciolli, V., Testa, U., Monetesoro, E., Bulgarini, D., Proietti, E., Borghi, P., Sestili, P., Locardi, C., and Peschle, C. (1989). Anti-tumor effects of interleukin-2 and interleukin-1 in mice transplanted with different syngeneic tumors. Int. J. Cancer 44(6): 1108-16.

39. A., Ivanov V. N. and Ronai Z. (2001). Activating transcription factor 2-derived peptides alter resistance of human tumor cell lines to ultraviolet irradiation and chemical treatment. Clin. Cancer Res. 7:331-342.

40. Boehm, U., Guethlein, L., Klamp, T., Ozbek, K., Schaub, A., Futterer, A., Pfeffer, K., and Howard, J. C. (1998). Two families of GTPases dominate the complex cellular response to IFN-gamma. J. Immunol. 161(12):6715-23.

41. Chen S. H., Shine H. D., Goodman J. C., Grossman R. G. and Woo S. L. (1994). Gene therapy for brain tumors; regression of experimental gliomas by adenovirus-mediated gene transfer in vivo. Proc. Natl. Acad. Sci. USA. 91(8):3054-7.

42. Chen S. H., Shine H. D., Goodman J. C., Grossman R. G. and Woo S. L. (1994). Gene therapy for brain tumors; regression of experimental gliomas by adenovirus-mediated gene transfer in vivo. Proc. Natl. Acad. Sci. USA. 91(8):3054-7

43. Castellano M. and Parmiani G. (1999). Genes involved in melanoma: an overview of INK4a and other loci. Melanoma Res. 9:421-432.

44. Cho S. G., Bhoumik A., Broday L., Ivanov V., Rosenstein B. and Ronai Z. (2001). TIP49b, a Regulator of Activating Transcription Factor 2 Response to Stress and DNA Damage. Mol. Cell. Biol. 21:8398-4813.

45. Czaja, M. J., Weiner, F. R., and Freedman, J. H. (1991). Amplification of the metallothionein-1 and metallothionein-2 genes in copper-resistant hepatoma cells. J. Cell Physiol. 147(3):434-8.

46. Daniel P. T., Wieder T., Sturm I. and Schulze-Osthoff K. (2001). The kiss of death: promises and failures of death receptors and ligands in cancer therapy. Leukemia 15:1022-1032.

46. de Vries, T. J., van Muijen, G. N., and Ruiter, D. J. (1996). The plasminogen activation system in melanoma cell lines and in melanocytic lesions. Melanoma Res. 6:79-88.

46. Di Christofano A., Kotsi P., Peng Y. F., Cordon-Cardo C., Elkon K. B. and Pandolfi P. P. (1999). Impaired Fas response and autoimmunity in Pten+/− mice. Science 285: 2122-2125.

46. Ekmekcioglu S., Okcu M. F., Colome-Grimmer M. I., Owen-Schaub L., Buzaid A. C. and Grimm E. A. (1999). Differential increase of Fas ligand expression on metastatic and thin or thick primary melanoma cells compared with interleukin-10. Melanoma Res. 9:261-272.

46. Fan M., Goodwin M., Vu T., Brantley-Finley C., Gaarde W. A. and Chambers T. C. (2000). Vinblastine-induced phosphorylation of Bcl-2 and Bcl-XL is mediated by JNK and occurs in parallel with inactivation of the Raf-1/MEK/ERK cascade. J. Biol. Chem. 275:29980-29985.

46. Ferrone S, and Marincola F. M. (1995). Loss of HLA class I antigens by melanoma cells: molecular mechanisms, functional significance and clinical relevance. Today 16:487-494.

46. Fuchs, S. Y., Xie, B., Adler, V. A., Fried, V. A., Davis, R. J., Ronai. Z. (1997) c-Jun $NH_2$—terminal kinases target the ubiquitination of their associated transcription factors. J. Biol. Chem. 272: 32163-32168, 46. Gopalkrishnan R. V., Christiansen K. A., Goldenstein N. I., DePinho R. A. and Fisher P. B. (1999). Use of the human EF-1alpha promoter for expression can significantly increase success in establishing stable cell lines with consistent expression: a study using the tetracycline-inducible system in human cancer cells. Nucleic Acids Res. 27(24): 4775-82.

46. Gossen M. and Bujard H. (1992). Tight control of genen expression in mammalian cells by tetracycline-responsive promoters. Proc. Natl. Acad. Sci. USA. 89(12):5547-51

46. Hai T. W., Liu F., Coukos W. J. and Green M. R. (1989). Transcription factor ATF cDNA clones: an extensive family of leucine zipper proteins able to selectively form DNA-binding heterodimers. Genes Dev. 3:2083-2090.

46. Hofbauer, G. F., Geertsen, R., Laine, E., Brug, G., and Dummer, R. (2001). Impact of interferons on the expression of melanoma-associated antigens in melanoma short-term cell cultures. Melanoma Res. 11(3):213-8.

46. Hofmann, U. B., Westphal, J. R., Van Muijen, G. N., and Ruiter, D. J. (2000). Matrix metalloproteinases in human melanoma. J. Invest Dermatol. 115(3):337-44.

46. Huguier S., Baguet J., Perez S., van Dam H. and Castellazzi M. (1998). Transcription factor ATF2 cooperates with v-Jun to promote growth factor-independent proliferation in vitro and tumor formation in vivo. Mol. Cell. Biol. 18:7020-7029.

46. Ivanov V. N., Bhoumik A., Krasilnikov M., Raz R., Owen-Schaub L. B., Levy D., Horvath C. M. and Ronai Z. (2001). Cooperation between STAT3 and c-jun suppresses Fas transcription. Mol. Cell. 7:517-528.

46. Ivanov V. N., Fodstad o. and Ronai Z. (2001). Expression of ring finger-deleted TRAF2 sensitizes metastatic melanoma cells to apoptosis via up-regulation of p38, TNFalpha and suppression of NF-kappaB activities. Oncogene 20:2243-2253

46. Jean D., Harbison M., McConkey D. J., Ronai Z. and Bar-Eli M. (1998). CREB and its associated proteins act as survival factors for human melanoma cells. J. Biol. Chem. 273:24884-24890.

46. Jean D., Tellez C., Huang S., Davis D. W., Bruns C. J., McConkey D. J., Hinrichs S. H. and Bar-Eli M. (2000). Inhibition of tumor growth and metastasis of human melanoma by intracellular anti-ATF-1 single chain Fv fragment. Oncogene 19:2721-2730.

46. Joneson T. and Bar-Sagi D. (1999). Suppression of Ras-induced apoptosis by the Rac GTPase. Mol. Cell. Biol. 19:5892-5901.

46. Kageshita T., Hamby C. V., Ishihara T., Matsumoto K., Saida T. and Ono T. (2001). Loss of beta-catenin expression associated with disease progression in malignant melanoma. Br. J. Dermatol. 145:210-216.

46. Kang, D., Jiang, H., Wu, Q., Pestka, S., and Fisher, P. B. (2001). Cloning and characterization of human ubiquitin-processing protease-43 from terminally differentiated human melanoma cells using rapid subtraction hybridization protocol RaSH. Gene 267(2):233-42.

46. Kaszubska W., Hooft van Huijsduijnen R., Ghersa P., DeRaemy-Schenk A. M., Chen B. P., Hai T., DeLamarter J. F. and Whelan J. (1993). Cyclic AMP-independent ATF family members interact with NF-kappa B and function in the activation of the E-selectin promoter in response to cytokines. Mol. Cell. Biol. 13:7180-7190.

46. Kim S. J., Wagner S., Liu F., O'Reilly M. A., Robbins P. D. and Green M. R. (1992). Retinoblastoma gene product activates expression of the human TGF-beta 2 gene through transcription factor ATF-2. Nature 358:331-334.

46. Li X. Y. and Green M. R. (1996). Intramolecular inhibition of activating transcription factor-2 function by its DNA-binding domain. Genes Dev. 10:517-527.

46. Liu F. and Green M. R. (1990). A specific member of the ATF transcription factor family can mediate transcription activation by the adenovirus E1a protein. Cell 61:1217-1224.

46. Maguire H. F., Hoeffler J. P. and Siddiqui A. (1991). HBV X protein alters the DNA binding specificity of CREB and ATF-2 by protein-protein interactions. Science 252:842-844.

46. Manning, B. D., and Snyder, M. (2000). Drivers and passengers wanted! The role of kinesin-associated proteins. Trends Cell Biol. 10(7):281-9.

46. Mashima, T., Udagawa. S., and Tsuruo, T. (2001). Involvement of transcriptional repressor ATF3 in acceleration of caspase protease activation during DNA damaging agent-induced apoptosis. J. Cell Physiol. 188(3):352-8.

46. Min W. and Pober J. S. (1997). TNF initiates E-selectin transcription in human endothelial cells through parallel TRAF-NF-kappa B and TRAF-RAC/CDC42-JNK-c-Jun/ATF2 pathways. J. Immunol. 159:3508-3518.

46. Minamoto T., Buschmann T., Habelhah H., Matusevich E., Tahara H., Boerresen-Dale A-L., Harris C., Sidransky D. and Ronai Z. (2001). Distinct pattern of p53 phosphorylation in human tumors. Oncogene 20:3341-3347.

46. Narayan S., Widen S. G., Beard W. A. and Wilson S. H. (1994). RNA polymerase II transcription. Rate of promoter clearance is enhanced by a purified activating transcription factor/cAMP response element-binding protein. J. Biol. Chem. 269:12755-12763.

46. Newell C. L., Deisseroth A. B. and Lopez-Berestein G. J. (1994). Interaction of nuclear proteins with an AP-1/CRE-like promoter sequence in the human TNF-alpha gene. Leukoc. Biol. 56:27-35.

46. Novak U., Paradiso L. and Hamilton J. A. (1994). Regulation of the urokinase gene by the retinoblastoma protein. DNA Cell Biol., 13:1063-1069.

46. Nyormoi O., Wang Z., Doan D., Ruiz M., McConkey D. and Bar-Eli M. (2001). Transcription factor AP-2alpha is preferentially cleaved by caspase 6 and degraded by proteasome during tumor necrosis factor alpha-induced apoptosis in breast cancer cells. Mol. Cell. Biol. 21:4856-4867.

46. Owen-Schaub L. B., van Golen K., Hill L. and Price J. E. (1998). Fas and Fas ligand interactions suppress melanoma lung metastasis. J. Exp. Med. 188:1717-1723.

46. Poetsch M., Dittberner T. and Woenckhaus C. (2001). PTEN/MMAC1 in malignant melanoma and its importance for tumor progression. Cancer Genet. Cytogenet. 125:21-26.

46. Raingeaud J., Whitmarsh A. J., Barrett T., Derijard B. and Davis R. J. (1996). MKK3- and MKK6 regulated gene expression is mediated by the p38 mitogen-activated protein kinase signal transduction pathway. Mol. Cell. Biol. 16:1247-1255.

46. Read M. A., Whitley M. Z., Gupta S., Pierce J. W., Best J., Davis R. J. and Collins T. (1997). Tumor necrosis factor alpha-induced E-selectin expression is activated by the nuclear factor-kappaB and c-JUN N-terminal kinase/p38 mitogen-activated protein kinase pathways. J. Biol. Chem. 272:2753-2761.

46. Reimold A. M., Grusby M. J., Kosaras B., Fries J. W., Mori R., Maniwa S., Clauss I. M., Collins T., Sidman R. L., Glimcher M. J. and Glimcher L. H. (1996). Chondrodysplasia and neurological abnormalities in ATF-2-deficient mice. Nature 379:262-265.

46. Rocco J. W. and Sidransky D. (2001) p16(MTS-1/CDKN2/INK4a) in cancer progression. Exp Cell Res. 264: 42-55.

46. Rutberg S. E., Goldstein I. M., Yang Y. M., Stackpole C. W. and Ronai Z. (1994). Expression and transcriptional activity of AP-1, CRE, and URE binding proteins in B16 mouse melanoma subclones. Mol. Carcinog. 10: 82-87.

46. Satyamoorthy K., Chehab N. H., Waterman M. J., Lien M. C., El-Deiry W. S., Herlyn M. and Halazonetis T. D. (2000). Expression and transcriptional activity of AP-1, CRE, and URE binding proteins in B16 mouse melanoma subclones. Cell Growth Differ. 11:467-474.

46. Sekimoto, T., Nakajima, K., Tachibana, T., Hirano, T., and Yoneda, Y. (1996). Interferon-gamma-dependent nuclear import of Stat1 is mediated by the GTPases activity of Ran/TC4. J. Biol. Chem. 271(49):31017-20.

46. Serrone L. and Hersey P. (1999). The chemoresistance of human malignant melanoma: an update. Melanoma Res. 9:51-58.

46. Shimizu M., Nomura Y., Suzuki H., Ichikawa E., Takeuchi A., Suzuki M., Nakamura T., Nakajima T. and Oda K. (1998). Activation of the rat cyclin A promoter by ATF2 and Jun family members and its suppression by ATF4. Exp. Cell Res. 239:93-103.

46. Singer, J. D., Gurian-West, M., Clurman, B., and Roberts, J. M. (1999). Cullin-3 targets cyclin E for ubiquitination and controls S phase in mammalian cells. Genes Dev. 13(18):2375-87.

46. Soengas M. S., Capodieci P., Polsky D., Mora J., Esteller M., Opitz-Araya X., McCombie R., Herman J. G., Gerald W. L., Lazebnik Y. A., Cordon-Cardo C. and Lowe S. W. (2001). Inactivation of the apoptosis effector Apaf-1 in malignant melanoma. Nature 409:207-211.

46. Soubrane C., Mouawad R., Antoine E. C., Verola O., Gil-Delgado M. and Khayat D. (2000). A comparative study of Fas and Fas-ligand expression during melanoma progression. Br. J. Dermatol. 143:307-312.

46. Symond H., Krall L., Remington L., Saenz-Robles M., Lowe S., Jacks T. and Van Dyke T. (1994). P53-dependent apoptosis suppresses tumor growth and progression in vivo. Cell. 78:703-11

46. Timokhina I., Kissel H., Stella G. and Besmer, P. (1998). Kit signaling through PI 3-kinase and Src kinase pathways: an essential role for Rac1 and JNK activation in mast cell proliferation. EMBO J. 17:6250-6262.

46. Tsai E. Y., Jain J., Pesavento P. A., Rao A. and Goldfeld A. E. (1996). Tumor necrosis factor alpha gene regulation in activated T cells involves ATF-2/Jun and NFATp. Mol. Cell. Biol. 16:459-467.

46. van Dam H., Duyndam M., Rottier R., Bosch A., de Vries-Smits L., Herrlich P., Zantema A., Angel P. and van der Eb A. J. (1993). Heterodimer formation of cJun and ATF-2 is responsible for induction of c-jun by the 243 amino acid adenovirus E1A protein. EMBO J. 12:479-487.

46. van Dam H., Wilhelm D., Herr I., Steffen A., Herrlich P. and Angel P. (1995). ATF-2 is preferentially activated by stress-activated protein kinases to mediate c-jun induction in response to genotoxic agents. EMBO J. 14:1798-1811.

46. Vunic D., Stennicke H. R., Pisabarro M. T., Salvesen G. S. and Dixit V. M. (2000). ML-IAP, a novel inhibitor of apoptosis that is preferentially expressed in human melanomas. Curr. Biol. 10:1359-1366.

46. Wagner S, and Green M. R. (1993). HTLV-I Tax protein stimulation of DNA binding of bZIP proteins by enhancing dimerization. Science 262:395-399.

100. Winston, J. T., Chu, C., and Harper, J. W. (1999). Culprits in the degradation of cyclin E apprehended. Genes Dev. 13: 2751-7.

101. Yamaguchi Y., Katah H., Mori K. and Negishi M. (2001). RhoA inhibits the nerve growth factor-induced Rac1 activation through Rho-associated kinase-dependent pathway. J. Biol. Chem. 276:18977-18983.

102. Yamazaki, H., Nakata, T., Okada, Y., Hirokawa, N. (1996). Cloning and characterizing of KAP3: a novel kinesin superfamily-associated protein of KIF3A/3B. Proc. Natl. Acad. Sci. USA 93.

103. Yang Y. M., Dolan L. R. and Ronai Z. (1996). Expression of dominant negative CREB reduces resistance to radiation of human melanoma cells. Oncogene 12:2223-2233.

104. Yang-Yen H. F., Chiu R. and Karin M. (1990). Elevation of AP1 activity during F9 cell differentiation is due to increased c-jun transcription. New Biol. 2:351-361.

I claim:

1. An isolated nucleic acid encoding a peptide consisting of an inhibitory N-terminal fragment of ATF-2, wherein the inhibitory N-terminal fragment of ATF2 is selected from the group consisting of:
   i. a peptide consisting of amino acid residues 1 to 115 of ATF-2;
   ii. a peptide consisting of amino acid residues 50 to 100 of ATF-2;
   iii. a peptide consisting of amino acid residues 45 to 75 of ATF-2;
   iv. a peptide consisting of amino acid residues 45 to 100 of ATF-2; and
   v. a peptide consisting of amino acid residues 50 to 75 of ATF2.

2. An isolated expression vector comprising the nucleic acid of claim 1 operably associated with an expression control sequence.

3. The expression vector of claim 2, wherein the expression control sequence provides for expression in a tumor cell.

4. A composition comprising the expression vector of claim 2 and a pharmaceutically acceptable carrier or excipient.

5. An isolated expression vector comprising the nucleic acid of claim 1 operably associated with a heterologous expression control sequence.

6. An isolated nucleic acid encoding a fusion protein comprising an inhibitory N-terminal fragment of ATF-2 and a heterologous polypeptide, wherein the inhibitory N-terminal fragment of ATF2 is selected from the group consisting of:

i. a peptide consisting of amino acid residues 1 to 115 of ATF-2;

ii. a peptide consisting of amino acid residues 50 to 100 of ATF-2;

iii. a peptide consisting of amino acid residues 45 to 75 of ATF-2;

iv. a peptide consisting of amino acid residues 45 to 100 of ATF-2; and v. a peptide consisting of amino acid residues 50 to 75 of ATF2.

* * * * *